United States Patent
Bassarab et al.

(10) Patent No.: US 11,897,964 B2
(45) Date of Patent: Feb. 13, 2024

(54) ANTI-PSGL-1 ANTIBODIES AND USES THEREOF

(71) Applicant: AltruBio Inc., Wilmington, DE (US)

(72) Inventors: Stefan Bassarab, Biberach an der Riss (DE); Barbara Enenkel, Warthausen (DE); Patrick Garidel, Norderstedt (DE); Heidrun Schott, Schemmerhofen (DE); Sanjaya Singh, Sandy Hook, CT (US); Tobias Litzenburger, Mittelbiberach (DE)

(73) Assignee: AltruBio Inc., Wilmington, DE (US)

( * ) Notice: Subject to any disclaimer, the term of this patent is extended or adjusted under 35 U.S.C. 154(b) by 0 days.

(21) Appl. No.: 17/460,883

(22) Filed: Aug. 30, 2021

(65) Prior Publication Data

US 2021/0395383 A1    Dec. 23, 2021

Related U.S. Application Data

(62) Division of application No. 13/494,398, filed on Jun. 12, 2012, now abandoned.

(60) Provisional application No. 61/496,249, filed on Jun. 13, 2011.

(51) Int. Cl.
  C07K 16/28    (2006.01)
  A61K 39/00    (2006.01)

(52) U.S. Cl.
  CPC .... *C07K 16/2896* (2013.01); *A61K 2039/505* (2013.01); *C07K 2317/24* (2013.01); *C07K 2317/53* (2013.01)

(58) Field of Classification Search
  None
  See application file for complete search history.

(56) References Cited

U.S. PATENT DOCUMENTS

| | | |
|---|---|---|
| 5,378,464 A | 1/1995 | McEver |
| 5,618,785 A | 4/1997 | Heavner et al. |
| 5,667,425 A | 9/1997 | Pineau et al. |
| 5,709,859 A | 1/1998 | Aruffo et al. |
| 5,710,123 A | 1/1998 | Heavner et al. |
| 5,808,025 A | 9/1998 | Tedder et al. |
| 5,827,817 A | 10/1998 | Larsen et al. |
| 5,834,425 A | 11/1998 | Tedder et al. |
| 5,840,679 A | 11/1998 | Larsen et al. |
| 5,843,707 A | 12/1998 | Larsen et al. |
| 5,852,175 A | 12/1998 | Cummings et al. |
| 5,866,124 A | 2/1999 | Hardman et al. |
| 5,972,625 A | 10/1999 | Rosen et al. |
| 6,056,956 A | 5/2000 | Cobbold et al. |
| 6,124,267 A | 9/2000 | McEver et al. |
| 6,177,547 B1 | 1/2001 | Cummings et al. |
| 6,210,671 B1 | 4/2001 | Co |
| 6,309,639 B1 | 10/2001 | Cummings et al. |
| 6,348,581 B1 | 2/2002 | Anderson et al. |
| 6,506,382 B2 | 1/2003 | Cummings et al. |
| 6,667,036 B2 | 12/2003 | Cummings et al. |
| 6,884,619 B2 | 4/2005 | Hockfield et al. |
| 7,387,777 B2 | 6/2008 | Wagner et al. |
| 7,563,441 B2 * | 7/2009 | Graus ................. A61P 7/02 424/152.1 |
| 7,604,800 B2 | 10/2009 | Lin et al. |
| 7,744,888 B2 | 6/2010 | Lin et al. |
| 8,283,450 B2 | 10/2012 | Kato et al. |
| 8,287,871 B2 | 10/2012 | Lin et al. |
| 8,298,540 B2 | 10/2012 | Lin et al. |
| 8,361,472 B2 | 1/2013 | Lin et al. |
| 8,557,579 B2 | 10/2013 | Lin et al. |
| 8,628,775 B2 | 1/2014 | Lin et al. |
| 8,663,641 B2 | 3/2014 | Lin et al. |
| 8,828,397 B2 | 9/2014 | Lin et al. |
| 9,494,574 B2 | 11/2016 | Lin et al. |
| 9,631,019 B2 | 4/2017 | Lin et al. |
| 10,030,075 B2 | 7/2018 | Lin et al. |
| 2002/0058034 A1 | 5/2002 | Manjunath et al. |
| 2002/0164336 A1 | 11/2002 | Harrison et al. |
| 2003/0049252 A1 | 3/2003 | Lin et al. |
| 2004/0001839 A1 | 1/2004 | Levanon et al. |
| 2004/0002450 A1 | 1/2004 | Lazarovits et al. |
| 2004/0116333 A1 | 6/2004 | Lin et al. |
| 2005/0266003 A1 | 12/2005 | Lin et al. |

(Continued)

FOREIGN PATENT DOCUMENTS

| | | |
|---|---|---|
| CA | 2681341 A1 | 9/2008 |
| CL | 2005000827 A1 | 2/2006 |

(Continued)

OTHER PUBLICATIONS

Stubenrauch et al., Drug Metabolism and Disposition 38: 84-91, 2010 (Year: 2010).*
Decision on Appeal No. 2020-000370, U.S. Appl. No. 13/494,398 mailed Sep. 25, 2020. (Year: 2020).*
International Search Report and Written Opinion for PCT/US2005/016357 dated Nov. 3, 2005.
International Search Report and Written Opinion dated Sep. 19, 2012 for PCT/US2012/042068.
[No Author Listed], Blast (Basic Local Alignment Search Tool). Accession No. AAH03874: Selectin, platelet (p-selectin) ligand . . . Last accessed on Apr. 27, 2010 at http://blast.ncbi.nlm.nih.gov/Blast.cgi . 4 pages.
[No Author Listed], CD162 (PL1). Monoclonal Antibody. Medical & Biological Laboratories Co., LTD. May 31, 2002. 2 pages.

(Continued)

*Primary Examiner* — Sharon X Wen
(74) *Attorney, Agent, or Firm* — Wolf, Greenfield & Sacks, P.C.

(57) ABSTRACT

Provided herein, in one aspect, are antibodies that immunospecifically bind to PSGL-1, polynucleotides comprising nucleotide sequences encoding such antibodies, and expression vectors and host cells for producing such antibodies. Also provided herein are kits and pharmaceutical compositions comprising antibodies that specifically bind to PSGL-1, as well as methods of treating a disorder or disease caused by or associated with increased proliferation and/or numbers of activated T cells using the antibodies described herein.

5 Claims, 7 Drawing Sheets

Specification includes a Sequence Listing.

(56) References Cited

U.S. PATENT DOCUMENTS

| | | | |
|---|---|---|---|
| 2006/0003940 | A1 | 1/2006 | Lin et al. |
| 2006/0073148 | A1 | 4/2006 | Tchistiakova et al. |
| 2009/0092614 | A1 | 4/2009 | Demarest et al. |
| 2009/0093002 | A1 | 4/2009 | Pfeifer et al. |
| 2009/0191204 | A1* | 7/2009 | Lin .................. A61P 35/00 435/375 |
| 2009/0198044 | A1 | 8/2009 | Lin et al. |
| 2009/0304709 | A1 | 12/2009 | Lin et al. |
| 2010/0080819 | A1 | 4/2010 | Lin et al. |
| 2010/0233157 | A1* | 9/2010 | Osorio .................. A61P 3/00 435/254.2 |
| 2010/0267934 | A1 | 10/2010 | Van de Winkel et al. |
| 2011/0086366 | A1* | 4/2011 | Labrijn ............ G01N 33/6854 436/501 |
| 2011/0172397 | A1 | 7/2011 | Lin et al. |
| 2011/0178270 | A1 | 7/2011 | Lin et al. |
| 2012/0183565 | A1* | 7/2012 | Mataraza .............. A61P 37/00 435/69.6 |
| 2013/0011861 | A1 | 1/2013 | Lin et al. |
| 2013/0101587 | A1 | 4/2013 | Lin et al. |
| 2013/0102762 | A1 | 4/2013 | Lin et al. |
| 2013/0209449 | A9 | 8/2013 | Bassarab et al. |
| 2013/0251708 | A1 | 9/2013 | Bassarab et al. |
| 2014/0065176 | A1 | 3/2014 | Lin et al. |
| 2015/0183870 | A1 | 7/2015 | Lin et al. |
| 2016/0051695 | A1 | 2/2016 | Lin et al. |
| 2017/0190782 | A1 | 7/2017 | Lin et al. |

FOREIGN PATENT DOCUMENTS

| | | |
|---|---|---|
| CL | 20050001081 A1 | 3/2006 |
| CL | 2005001485 A1 | 7/2006 |
| CL | 2008003089 A1 | 1/2009 |
| CL | 2012000254 A1 | 4/2013 |
| CN | 1473052 A | 2/2004 |
| CN | 101331150 A | 12/2008 |
| EP | 1 707 627 A1 | 10/2006 |
| JP | 2007-536933 A | 12/2007 |
| JP | 2008-508852 A | 3/2008 |
| KR | 10-0891620 B1 | 4/2009 |
| TW | 200536860 A | 7/2013 |
| WO | WO 97/06176 A2 | 2/1997 |
| WO | WO 00/25808 A1 | 5/2000 |
| WO | WO 01/83806 A1 | 11/2001 |
| WO | WO 02/022820 A1 | 3/2002 |
| WO | WO 02/053700 A2 | 7/2002 |
| WO | WO 2002/100330 A2 | 12/2002 |
| WO | WO 03/013603 A1 | 2/2003 |
| WO | WO 2004/003166 A2 | 1/2004 |
| WO | WO 2005/005455 A2 | 1/2005 |
| WO | WO 2005/027831 A2 | 3/2005 |
| WO | WO 2005/080586 A1 | 3/2005 |
| WO | WO 2005/100402 A1 | 10/2005 |
| WO | WO 2005/110456 A2 | 11/2005 |
| WO | WO 2005/110475 A2 | 11/2005 |
| WO | WO 2006/029879 A2 | 3/2006 |
| WO | WO 2008/119353 A1 | 10/2008 |
| WO | WO 2009/032145 A1 | 3/2009 |
| WO | WO 2009/052439 A2 | 4/2009 |
| WO | WO 2009/103791 A1 | 8/2009 |
| WO | WO-2009140623 A2 * | 11/2009 ............ A61P 1/04 |
| WO | WO 2010/070346 A2 | 6/2010 |
| WO | WO 2010/102792 A1 | 9/2010 |
| WO | WO 2011/014438 A1 | 2/2011 |
| WO | WO 2012/174001 A1 | 12/2012 |

OTHER PUBLICATIONS

[No Author Listed], CD162 (PL2). Monoclonal Antibody. Medical & Biological Laboratories Co., LTD. May 31, 2002. Last accessed online Oct. 6, 2011 at http://www.mblintl.com/sites/default/files/datasheets/K0037-3.pdf. 1 page.

[No Author Listed], Immunoglobulin G (IgG) engineering: mutant Fc regions for altered properties or increased half-life. Engineered Fc Regions Review. InvivoGen. 2011 (month not listed on publication). Retrieved from www.invivogen.com/review-engineered-pfuse-chig. 3 pages.

[No Author Listed], Phase IIa Study of Multiple Doses of AbGn-168H by IV Infusion in Moderate to Severe Chronic Plaque Psoriasis Patients (AbGn-168H), ClinicalTrials.gov Identifier: NCT01855880, May 17, 2013, 8 pages. Accessed online: https://www.clinicaltrials.gov/ct2/show/NCT01855880?term=AbGn-168H&draw=2&rank=2.

[No Author Listed], Product details for anti-CD162/PSGL-1 (clone PL2) antibody. Antibodies-online.com. 3 pages. Last accessed online Jul. 1, 2011 at http://www.antibodies-online.com/productsheets/en/ABIN131576.pdf.

[No Author Listed], Purified Mouse Anti-Human CD162. Technical Data Sheet. BD Pharmingen. 2006. 2 pages.

[No Author Listed], Safety, Tolerability, Pharmacokinetics and Pharmacodynamics of Single Doses of AbGn-168 in Psoriasis. Sponsored by Boehringer Ingelheim Pharmaceuticals. Last accessed on Aug. 28, 2009 at http://clinicaltrials.gove/ct2/show/NCT00848055?cond=psoriasis&spons . . . Study Start Date: Dec. 2008. 3 pages.

Aalberse et al., IgG4 breaking the rules. Immunology. Jan. 2002;105(1):9-19.

Aalberse et al., The apparent monovalency of human IgG4 is due to bispecificity. Int Arch Allergy Immunol. Feb.-Apr. 1999;118(2-4):187-9.

Abedin et al., Neihulizumab (ABGN-168H) In Patients With Steroid-Refractory Acute Graft-versus-Host-Disease (SR-AGVHD): Preliminary Results Of A Phase I Study, European Hematology Association (Abstract), 2020. 1 page.

Abedin et al., Neihulizumab (ABGN-168H) In Patients With Steroid-Refractory Acute Graft-versus-Host-Disease (SR-AGVHD): Preliminary Results Of A Phase I Study, European Hematology Association Poster, 2020. 1 page.

Angal et al., A single amino acid substitution abolishes the heterogeneity of chimeric mouse/human (IgG4) antibody. Mol Immunol. Jan. 1993;30(1):105-8.

Associate Summary of Opposition dated Oct. 10, 2014 in Colombian Application No. 14004726.

Ball et al., Antibody C region influences TGN1412-like functional activity in vitro. J Immunol. Dec. 15, 2012;189(12):5831-40. Epub Nov. 12, 2012.

Battistini et al., CD8+ T cells from 1-37 patients with acute multiple sclerosis display selective increase of adhesiveness in brain venules: A critical role for P-selectin glycoprotein ligand-1. Blood. Jun. 15, 2003;101(12):4775-82. Epub Feb. 20, 2003.

Beckwith et al., The protein product of the proto-oncogene c-cbl forms a complex with phosphatidylinositol 3-kinase p85 and CD19 in anti-igm stimulated human B-lymphoma cells. Blood. Nov. 1, 1996;88(9):3502-7.

Besnault et al., B cell receptor cross-linking triggers a caspase-8-dependent apoptotic pathway that is independent of the death effector domain of Fas-associated death domain protein. J Immunol. Jul. 15, 2001;167(2):733-40.

Bloom et al., Intrachain disulfide bond in the core hinge region of human IgG4. Protein Sci. Feb. 1997;6(2):407-15.

Borges et al., P-selectin glycoprotein ligand-1 (PSGL-1) on T helper 1 but not on T helper 2 cells binds to P-selectin and supports migration into inflamed skin. J Exp Med. Feb. 3, 1997;185(3):573-8.

Borges et al., The binding of T cell-expressed P-selectin glycoprotein ligand-1 to E- and P-selectin is differentially regulated. J Biol Chem. Nov. 7, 1997;272(45):28786-92.

Brown et al., Tolerance of single, but not multiple, amino acid replacements in antibody Vh Cdr 2: a means of minimizing B cell wastage from somatic hypermutation? J Immunol. May 1, 1996;156(9):3285-91.

Casset et al., A peptide mimetic of an anti-CD4 monoclonal antibody by rational design. Biochem Biophys Res Commun. Jul. 18, 2003;307(1):198-205.

(56) References Cited

OTHER PUBLICATIONS

Chang et al., Effective therapy of human lymphoma xenografts with a novel recombinant ribonuclease/anti-CD74 humanized IgG4 antibody immunotoxin. Blood. Dec. 15, 2005;106(13):4308-14. Epub Aug. 18, 2005.
Chen et al., Cross-linking of P-selectin glycoprotein ligand-1 induces death of activated T cells. Blood. Nov. 15, 2004;104(10):3233-42. Epub Jun. 15, 2004.
Co et al., Chimeric and humanized antibodies with specificity for the CD33 antigen. J Immunol. Feb. 15, 1992;148(4):1149-54.
Co et al., Properties and pharmacokinetics of two humanized antibodies specific for L-selectin. Immunotechnology. Mar. 1999;4(3-4):253-66.
Cohen et al., Efficacy and Safety of Neihulizumab (AbGn-168H) in Patients with Active Psoriatic Arthritis: 24-week Results from a Phase II Open Label Study, Abstract No. 906017, ACR Convergence Poster, 2020. 1 page.
Colman, Effects of amino acid sequence changes on antibody-antigen interactions. Res Immunol. Jan. 1994;145(1):33-6.
Diacovo et al., Interactions of human alpha/beta and gamma/delta T lymphocyte subsets in shear flow with E-selectin and P-selectin. J Exp Med. Mar. 1996;183:1193-1203.
Dimitroff et al., Glycosylation-dependent inhibition of cutaneous lymphocyte-associated antigen expression: Implications in modulating lymphocyte migration to skin. Blood. Jan. 15, 2003;101(2):602-10.
Edelman et al., The covalent structure of an entire gammaG immunoglobulin molecule. Proc Natl Acad Sci U S A. May 1969;63(1):78-85.
Ellison et al., Linkage and sequence homology of two human immunoglobulin gamma heavy chain constant region genes. Proc Natl Acad Sci U S A. Mar. 1982;79(6):1984-8.
Ellison et al., The nucleotide sequence of a human immunoglobulin C gammal gene. Nucleic Acids Res. Jul. 10, 1982;10(13):4071-9.
Evangelista et al., Platelet/polymorphonuclear leukocyte interaction: P-selectin triggers protein-tyrosine phosphorylation-dependent CD11b/CD18 adhesion: Role of PSGL-1 as a signaling molecule. Blood. Feb. 1, 1999;93(3):876-85.
Faraday et al., Leukocytes can enhance platelet-mediated aggregation and thromboxane release via interaction of P-selectin glycoprotein ligand 1 with P-selectin. Anesthesiology. Jan. 2001;94(1):145-51.
Frankel et al., Characterization of diphtheria fusion proteins targeted to the human interleukin-3 receptor. Protein Eng. Aug. 2000;13(8):575-81.
Frenette et al., P-selectin glycoprotein ligand 1 (PSGL-1) is expressed on platelets and can mediate platelet-endothelial interactions in vivo. J Exp Med. Apr. 17, 2000;191(8):1413-22.
Fuhlbrigge et al., Cutaneous lymphocyte antigen is a specialized form of PSGL-1 expressed on skin-homing T cells. Nature. Oct. 1997;389:978-81.
GenBank Accession No. AAA38463, downloaded Nov. 2, 2009.
GenBank Accession No. AAH29782, Selectin P ligand [Homo sapiens], originally posted May 20, 2002.
GenBank Accession No. AAO19056, downloaded Nov. 2, 2009.
GenBank Accession No. AAQ74699, downloaded Nov. 2, 2009.
Genbank Submission; Database EMBL, Accession No. AF045490; O'Conner et al.; first submitted to EMBL Feb. 2, 1998; 2 pages.
Graser et al., Identification of a CD8 T cell that can independently mediate autoimmune diabetes development in the complete absence of CD4 T cell helper functions. J Immunol. Apr. 1, 2000;164(7):3913-8.
Griffiths et al., Psoriasis, T cells and autoimmunity. J R Soc Med. Jun. 1996;89(6):315-9.
He et al., Humanization and pharmacokinetics of a monoclonal antibody with specificity for both E- and P-selectin. J Immunol. Jan. 15, 1998;160(2):1029-35.
Herron et al., Intracellular parasitism by the human granulocytic ehrlichiosis bacterium through the P-selectin ligand, PSGL-1. Science. Jun. 2, 2000;288(5471): 1653-6.

Hieter et al., Cloned human and mouse kappa immunoglobulin constant and J region genes conserve homology in functional segments. Cell. Nov. 1980;22(1 Pt 1):197-207.
Hirata et al., P-selectin glycoprotein ligand 1 (PSGL-1) is a physiological ligand for E- selectin in mediating t helper 1 lymphocyte migration. J Exp Med. Dec. 4, 2000;192(11):1669-75.
Hirose et al., A functional epitope on P-selectin that supports binding of P-selectin to P- selectin glycoprotein ligand-1 but not to sialyl Lewis X oligosaccharides. Internatl Immunol. Jan. 26, 1998;10(5):639-49.
Huang et al., A novel apoptosis-inducing anti-PSGL-1 antibody for T cell-mediated diseases. Eur J Immunol. 2005;35(7):2239-49.
Hwang et al., GlyCAM-1, a physiologic ligand for L-selectin, activates beta 2 integrins on naive peripheral lymphocytes. J Exp Med. Oct. 1, 1996;184(4):1343-8.
Igarashi et al., Telomerase activity is induced in human peripheral B lymphocytes by the stimulation to antigen receptor. Blood. 1997;89(4):1299-1307.
Kai et al., Switching constant domains enhances agonist activities of antibodies to a thrombopoietin receptor. Nat Biotechnol. Feb. 2008;26(2):209-11. Epub Dec. 23, 2007.
Kaytes et al., P-selectin mediates adhesion of the human melanoma cell line NKI-4: Identification of glycoprotein ligands. Biochemistry. Jul. 21, 1998;37(29): 10514-21.
Kieffer et al., Neutrophilis, monocytes, and dendritic cells express the same specialized form of PSGL-1 as do skin-homing memory T cells: Cutaneous lymphocyte antigen. Biochem Biophys Res Comm. Jul. 20, 2001;285(3):577-87.
Labrijn et al., Therapeutic IgG4 antibodies engage in Fab-arm exchange with endogenous human IgG4 in vivo. Nat Biotechnol. Aug. 2009;27(8):767-71. Epub Jul. 20, 2009.
Laszik et al., P-selectin glycoprotein ligand-1 is broadly expressed in cells of myeloid, lymphoid, and dendritic lineage and in some nonhematopoietic cells. Blood. Oct. 15, 1996;88(8):3010-21.
Levesque et al., PSGL-1-mediated adhesion of human hematopoietic progenitors to P-selectin results in suppression of hematopoiesis. Immunity. Sep. 1999;11:369-78.
Li et al., Visualization of P-selectin glycoprotein ligand-1 as a highly extended molecule and mapping of protein epitopes for monoclonal antibodies. J Biol Chem. 1996;271(11):6342-8.
Lund et al., Human Fc gamma RI and Fc gamma RII interact with distinct but overlapping sites on human IgG. J Immunol. Oct. 15, 1991;147(8):2657-62.
Mccloskey et al., Human constant regions influence the antibody binding characteristics of mouse-human chimeric IgG subclasses. Immunology. Jun. 1996;88(2):169-73.
Moiseenko, Monoclonal antibodies in treatment of cancer tumors. Practical Oncology. 2003; 4(3):148-156.
Moore et al., P-selectin glycoprotein ligand-1 mediates rolling of human neutrophils on P-selectin. J Cell Biol. 1995;128(4):661-71.
Newman et al., Modification of the Fc region of a primatized IgG antibody to human CD4 retains its ability to modulate CD4 receptors but does not deplete CD4(+) T cells in chimpanzees. Clin Immunol. Feb. 2001;98(2): 164-74.
Nirula et al., What is IgG4? A review of the biology of a unique immunoglobulin subtype. Curr Opin Rheumatol. Jan. 2011;23(1):119-24. Review. Erratum in: Curr Opin Rheumatol. Mar. 2011;23(2):227. Taylora, Frederick R [corrected to Taylor, Frederick R].
Norman et al., Leukocyte rolling in vivo is mediated by P-selectin glycoprotein ligand-1. Blood. Dec. 15, 1995;86(12):4417-21.
Paul, Fundamental Immunology: Third Edition. 1993. William E. Paul, M.D. Ed. Raven Press, New York. Chapter 9: pp. 292-295.
Queen et al., A humanized antibody that binds to the interleukin 2 receptor. Proc Natl Acad Sci USA. Dec. 1989;86(24):10029-33.
Royt et al., High and low spatial complimentarity. Immunology. 2000. Translated from Russian. p. 151.
Rubin et al., Phase II open label, single arm, multiple dose study of Neihulizumab, an anti CD162 (PSGL 1) antibody, in patients with moderate to severe active, anti TNFα and/or anti integrin refractory ulcerative colitis, Abstract No. 3346770, Digestive Disease Week (DDW) Poster, 2020. 1 page.

(56) References Cited

OTHER PUBLICATIONS

Rubin et al., A Phase II open label study of Neihulizumab, anti-CD162 (PSGL-1) antibody, in patients with moderately to severely active, anti-TNFα and/or anti-Integrin refractory ulcerative colitis, (Summary) 2020, 2 pages.

Rudikoff et al., Single amino acid substitution altering antigen-binding specificity. Proc Natl Acad Sci USA. 1982;79:1979-83.

Sako et al., Expression cloning of a functional glycoprotein ligand for P-selectin. Cell. Dec. 17, 1993;75(6):1179-86.

Samaranayake et al., Challenges in monoclonal antibody-based therapies. Ann Med. 2009;41(5):322-31. doi: 10.1080/07853890802698842.

Sayegh et al., The role of T-cell costimulatory activation pathways in transplant rejection. N Engl J Med. Jun. 18, 1998;338(25):1813-21.

Schuurman et al., The inter-heavy chain disulfide bonds of IgG4 are in equilibrium with intra-chain disulfide bonds. Mol Immunol. Jan. 2001;38(1):1-8.

Sela-Culang et al., The structural basis of antibody-antigen recognition. Front Immunol. Oct. 8, 2013;4:302. doi: 10.3389/fimmu.2013.00302.

Shan et al., Apoptosis of malignant human B cells by ligation of CD20 with monoclonal antibodies. Blood. 1998;91(5):1644-52.

Singer et al., The genetic molecules. Genes and Genomes. vol. 1; 1998. Chapter 1: 63, 66.

Snapp et al., A novel P-selectin glycoprotein ligand-1 monoclonal antibody recognizes an epitope within the tyrosine sulfate motif of human PSGL-1 and blocks recognition of both P-and L-selectin. Blood. Jan. 1, 1998;91(1): 154-64.

Stockmeyer et al., Polymorphonuclear granulocytes induce antibody-dependent apoptosis in human breast cancer cells. J Immunol. 2003; 171:5124-9.

Strausberg et al., Generation and initial analysis of more than 15,000 full-length human and mouse cDNA sequences. Proc Natl Acad Sci U S A. Dec. 24, 2002;99(26):16899-903. Epub Dec. 11, 2002.

Stubenrauch et al., Impact of molecular processing in the hinge region of therapeutic IgG4 antibodies on disposition profiles in cynomolgus monkeys. Drug Metab Dispos. Jan. 2010;38(1):84-91. Epub Oct. 22, 2009.

Suntharalingam et al. Cytokine storm in a phase 1 trial of the anti-CD28 monoclonal antibody TGN1412. N Engl J Med. Sep. 7, 2006;355(10):1018-28. Epub Aug. 14, 2006.

Thatte et al., Binding of function-blocking mAbs to mouse and human P-selectin glycoprotein ligand-1 peptides with and without tyrosine sulfation. J Leukoc Biol. Sep. 2002;72(3):470-7.

Trembleau et al., Pancreas-infiltrating Th1 cells and diabetes develop in IL-12 deficient nonobese diabetic mice. J Immunol. 1999;163:2960-8.

Vachino et al., P-selectin glycoprotein ligand-1 is the major counter-receptor for P-selectin on stimulated T cells and is widely distributed in non-functional form on many lymphocytic cells. J Biol Chem. Sep. 15, 1995;270(37):21966-74.

Vajdos et al., Comprehensive functional maps of the antigen-binding site of an anti-ErbB2 antibody obtained with shotgun scanning mutagenesis. J Mol Biol. Jul. 5, 2002;320(2):415-28.

Valdimarsson et al., Psoriasis: a T-cell-mediated autoimmune disease induced by streptococcal superantigens? Immunol Today. Mar. 1995;16(3):145-9.

Van Der Neut Kolfschoten et al., Anti-inflammatory activity of human IgG4 antibodies by dynamic Fab arm exchange. Science. Sep. 14, 2007;317(5844):1554-7.

Van Montfrans et al., Immunotherapy of Crohn's disease. Mediators Inflamm. 1998;7(3):149-52.

Veldman et al., Genomic organization and chromosomal localization of the gene encoding human P-selectin glycoprotein ligand. J Biol Chem. Jul. 7, 1995;270(27):16470-5.

Wang et al., Antibody structure, instability, and formulation. J Pharm Sci. Jan. 2007;96(1):1-26.

Wines et al., The IgG Fc contains distinct Fc receptor (FcR) binding sites: the leukocyte receptors Fc gamma RI and Fc gamma RIIa bind to a region in the Fc distinct from that recognized by neonatal FcR and protein A. J Immunol. May 15, 2000;164(10):5313-8.

Wing et al., Mechanism of first-dose cytokine-release syndrome by Campath 1-H: Involvement of CD16 (FcγRIII) and CD11a/CD18 (LFA-1) on NK cells. J Clin Invest 1996;98(12):2819-26.

Woltmann et al., Interleukin-13 induces PSGL-1/P-selectin-dependent adhesion of eosinophils, but not neutrophils, to human umbilical vein endothelial cells under flow. Blood. May 15, 2000;95(10): 3146-52.

Wu et al., Role of P-selectin and anti-P-selectin monoclonal antibody in apoptosis during hepatic/renal ischemia reperfusion injury. World J Gastroentero. 2000;6(2):244-7.

Xu et al., Diversity in the CDR3 region of V(H) is sufficient for most antibody specificities. Immunity. Jul. 2000;13(1):37-45.

Yago et al., IL-12 Promotes the adhesion of NK cells to endothelial selectins under flow conditions. J Immunol. 1998;161:1140-45.

Yang et al., Targeted gene disruption demonstrates that P-selectin glycoprotein ligand 1 (PSGL-1) is required for P-selectin-mediated but not E-selectin-mediated neutrophil rolling and migration. J Exp Med. Dec. 20, 1999;190(12):1769-82.

Yang et al., The biology of P-selectin glycoprotein ligand-1: its role as a selectin counterreceptor in leukocyte-endothelial and leukocyte-platelet interaction. Thrombosis Haemostasis. 1999;81(1):1-7.

Young, Preparing dermatology nurses: biologic therapy for psoriasis. Dermatology Nursing. 2003;15(5):11 pages. Retrieved from http://www.medscape.com/viewarticle/464020 on Jul. 12, 2013.

* cited by examiner

A. Heavy Chain

```
     {(Variable Region)   FR1              CDR1            FR2
  1  EVQLVESGGG LVQPGGSLRL SCAASGFTFS SFGMH|WVRQA PGKGLEWVA|Y
         CDR2                       FR3
 51  |INGGSSTIFY ANAVKG|RFTI SRDNAKNTLY LQMNSLRAED TAVYYCAR|YA
         CDR3          FR4      }{
101  |SYGGGAMDY|W GQGTLVTVSS ASTKGPSVFP LAPCSRSTSE STAALGCLVK 151  DYFPEPVTVS WNSGALTSGV HTFPAVLQSS GLYSLSSVVT VPSSSLGTKT
                           (Hinge Region)
201  YTCNVDHKPS NTKVDKRV |ES KYGPPCPPCP A|PEFLGGPSV FLFPPKPKDT
                         (Constant Region)
251  LMISRTPEVT CVVVDVSQED PEVQFNWYVD GVEVHNAKTK PREEQFNSTY

301  RVVSVLTVLH QDWLNGKEYK CKVSNKGLPS SIEKTISKAK GQPREPQVYT

351  LPPSQEEMTK NQVSLTCLVK GFYPSDIAVE WESNGQPENN YKTTPPVLDS
                                                           }
401  DGSFFLYSRL TVDKSRWQEG NVFSCSVMHE ALHNHYTQKS LSLSLGK
```

B. Light Chain

```
     {    FR1    (Variable Region)   CDR1            FR2
  1  DIQMTQSPSS LSASVGDRVT ITC|RSSQSIV HNDGNTYFE|W YQQKPGKAPK
         CDR2                    FR3                    CDR3
 51  LLIY|KVSNRF S|GVPSRFSGS GSGTHFTLTI SSLQPEDFAT YYC|FQGSYVP
         FR4       }{
101  |LT|FGQGTKVE IKR|TVAAPSV FIFPPSDEQL KSGTASVVCL LNNFYPREAK
                         (Constant Region)
151  VQWKVDNALQ SGNSQESVTE QDSKDSTYSL SSTLTLSKAD YEKHKVYACE
                        }
201  VTHQGLSSPV TKSFNRGEC
```

FIG. 7A – 7B

ANTI-PSGL-1 ANTIBODIES AND USES THEREOF

1. RELATED APPLICATIONS

This application is a divisional of and claims priority under 35 U.S.C. § 120 to U.S. patent application U.S. Ser. No. 13/494,398, filed Jun. 12, 2012, which claims the benefit of the filing date of U.S. provisional patent application 61/496,249, filed Jun. 13, 2011, entitled "ANTI-PSGL-1 ANTIBODIES AND USES THEREOF". The entire teachings and contents of the referenced applications are incorporated herein by reference.

2. FIELD

Provided herein are antibodies that specifically bind to P-selectin glycoprotein ligand-1 (PSGL-1), polynucleotides encoding such antibodies, expression vectors comprising such polynucleotides, host cells comprising such expression vectors, and related compositions. Also provided herein are methods for treating a disorder or a disorder caused by or associated with increased proliferation and/or numbers of activated T cells, such as psoriasis, using anti-PSGL-1 antibodies.

3. BACKGROUND

Inflammatory responses to infection or injury are initiated by the adherence of leukocytes to the vascular wall (McEver et al., 1997, J. Clin. Invest., 100 (3): 485-492). Selectins represents a family of glycoproteins which mediate the first leukocyte-endothelial cell and leukocyte-platelet interactions during inflammation. The selectin family, which consists of L-selectin, E-selectin, and P-selectin, comprise an $NH_2$-terminal lectin domain, followed by an EGF-like domain, a series of consensus repeats, a transmembrane domain, and a short cytoplasmic tail. The lectin domains of selectins interact with specific glycoconjugate ligands in order to facilitate cell adhesion. L-selectin, expressed on most leukocytes, binds to ligands on some endothelial cells and other leukocytes. E-selectin, expressed on cytokine activated endothelial cells, binds to ligands on most leukocytes. P-selectin, expressed on activated platelets and endothelial cells, also binds to ligands on most leukocytes.

P-selectin glycoprotein ligand-1 ("PSGL-1"), also known as SELPLG or CD162 (cluster of differentiation 162) is a human mucin-type glycoprotein ligand for all three selectins (Constantin, Gabriela, 2004, Drugs News Perspect, 17(9): 579-585; McEver et al., 1997, J. Clin. Invest., 100 (3): 485-492). PSGL-1 is a disulfide-bonded homodimer with two 120-kD subunits and is expressed on the surface of monocytes, lymphocytes, granulocytes, and in some $CD34^+$ stem cells. PSGL-1 is likely to contribute to pathological leukocyte recruitment in many inflammatory disorders since it facilitates the adhesive interactions of selectins, suggesting that inhibitors of PSGL-1, such as antibodies to PSGL-1, are potentially useful anti-inflammatory drugs.

Several anti-PSGL-1 antibodies have been developed (see, e.g., International Application Pub. No. WO 2005/110475, published Nov. 24, 2005; International Application Pub. No. WO 2003/013603, published Feb. 20, 2003; Constantin, Gabriela, 2004, Drugs News Perspect, 17(9): 579-585).

4. SUMMARY

In one aspect, provided herein are antibodies and antibody derived antigen-binding fragments that specifically bind to PSGL-1. In one embodiment, provided herein is a monoclonal antibody which immunospecifically binds to human PSGL-1 comprising: (i) a variable light ("VL") chain region comprising the amino acid sequence of SEQ ID NO: 3; (ii) a heavy chain comprising a variable heavy ("VH") chain region comprising the amino acid sequence of SEQ ID NO: 4; and (iii) a human IgG4 constant region which contains a Serine to Proline substitution at amino acid 228 of the heavy chain numbered according to the EU (gamma-G1 immunoglobulin) index (See, Edelman et al., 1969, Proc. Natl. Acad. Sci. USA, 63(1): 78-85). In a specific embodiment, provided herein is a monoclonal antibody which immunospecifically binds to human PSGL-1 comprising: (i) a light chain comprising the amino acid sequence of SEQ ID NO: 1; and (ii) a heavy chain comprising the amino acid sequence of SEQ ID NO: 2. In another specific embodiment, provided herein is a monoclonal antibody which immunospecifically binds to human PSGL-1 comprising: (i) a heavy chain consisting of SEQ ID NO: 2; and (ii) a light chain consisting of SEQ ID NO: 1. In another specific embodiment, provided herein is a monoclonal antibody which immunospecifically binds to human PSGL-1 comprising a heavy chain that comprises the amino acid sequence of SEQ ID NO: 2, and a complementary light chain. In a specific embodiment, any one of the foregoing monoclonal antibodies is purified.

In another aspect, provided herein is a pharmaceutical composition comprising any one of the foregoing monoclonal antibodies and a pharmaceutically acceptable carrier. In a specific embodiment, the pharmaceutical composition comprises a monoclonal antibody that is purified.

In one embodiment, provided herein is a pharmaceutical preparation comprising any one of the foregoing monoclonal antibodies in an aqueous solution comprising sodium citrate, sodium chloride, and citric acid monohydrate. In a specific embodiment, the pharmaceutical preparation is an aqueous solution comprising 9.1 mM sodium citrate dihydrate, 150 mM sodium chloride, and 0.9 mM citric acid. In another specific embodiment, the monoclonal antibody is present at a concentration of 0.267 mM in the pharmaceutical preparation. In a specific embodiment, the pharmaceutical preparation is an aqueous solution comprising 2.676 g/L sodium, 8.766 g/L sodium chloride, 0.2 g/L polysorbate 80, and 0.189 g/L citric acid. In another specific embodiment, the monoclonal antibody is present at a concentration of 40 g/L in the pharmaceutical preparation. In a specific embodiment, all the foregoing aqueous solutions are at pH 6.0.

In another aspect, provided herein are polynucleotides encoding an antibody described herein or an antigen-binding fragment thereof. In a specific embodiment, provided herein is an isolated polynucleotide encoding an antibody heavy chain comprising SEQ ID NO: 2. In an embodiment, an expression vector comprises the foregoing isolated polynucleotide. In certain embodiments, the expression vector further comprises a polynucleotide encoding an antibody light chain comprising SEQ ID NO:1. In a specific embodiment, the expression vector is a mammalian expression vector. In another aspect, provided herein is a host cell comprising a foregoing expression vector. In a specific embodiment, the host cell comprises (a) a first nucleic acid encoding SEQ ID NO: 2, operably linked to a promoter functional in said host cell; and (b) a second nucleic acid encoding SEQ ID NO: 1 operably linked to a promoter functional in said host cell. In another specific embodiment, the first and second nucleic acids of the host cell are in the same expression vector or in different expression vectors.

In another aspect, provided herein is a method of producing any of the foregoing monoclonal antibodies comprising culturing any of the foregoing host cells such that said first and second nucleic acids are expressed by said cell, and said heavy and light chains assemble together to form said antibody.

In another aspect, provided herein is an antibody heavy chain comprising SEQ ID NO: 2 or an antibody heavy chain fragment comprising amino acids 1 to 228 of SEQ ID NO:2. In a specific embodiment, provided herein is an antibody heavy chain comprising SEQ ID NO: 2. In another specific embodiment, provided herein is an antibody heavy chain fragment comprising amino acids 1 to 228 of SEQ ID NO:2. Also provided herein is a method of producing the foregoing heavy chain comprising culturing any of the foregoing host cells such that said heavy chain is expressed by the cell, and isolating said heavy chain. In a specific embodiment, a method of producing any of the foregoing antibodies comprises producing the heavy chain according to the forgoing method for producing the heavy chain, isolating said heavy chain, and complexing said heavy chain to an antibody light chain comprising SEQ ID NO:1.

In another aspect, provided herein is a kit comprising a first container containing any of the foregoing monoclonal antibodies. In a specific embodiment, the first container is a vial containing said monoclonal antibody as a lyophilized sterile powder under vacuum, and the kit further comprises a second container comprising a pharmaceutically acceptable fluid. Also provided herein is an injection device containing any of the foregoing monoclonal antibodies. In a specific embodiment, the injection device is a syringe.

In another aspect, provided herein are methods for preventing and/or treating a disease or disorder associated with or caused (in whole or part) by increased and/or numbers of activated T cells relative to healthy individuals or individuals not having the particular disease or disorder. In a specific embodiment, provided herein is a method for treating an inflammatory disorder, comprising administering to a subject in need thereof a therapeutically effective amount of any of the foregoing monoclonal antibodies. In another specific embodiment, a method for treating an inflammatory disorder, comprises administering to a subject in need thereof a therapeutically effective amount of any of the foregoing pharmaceutical compositions. In a specific embodiment, the inflammatory disorder is an autoimmune disease. In another specific embodiment, the inflammatory disorder is psoriasis. In another specific embodiment, the inflammatory disorder is plaque psoriasis. In another specific embodiment, the plaque psoriasis is moderate to severe. In another specific embodiment, the inflammatory disorder is erythrodermic psoriasis. In another specific embodiment, the inflammatory disorder is psoriatic arthritis. In another specific embodiment, the inflammatory disorder is rheumatoid arthritis. In another specific embodiment, the inflammatory disorder is Crohn's disease. In another specific embodiment, the inflammatory disorder is ankylosing spondylitis. In another specific embodiment, the inflammatory disorder is diabetes.

5. BRIEF DESCRIPTION OF THE FIGURES

Figure 3:
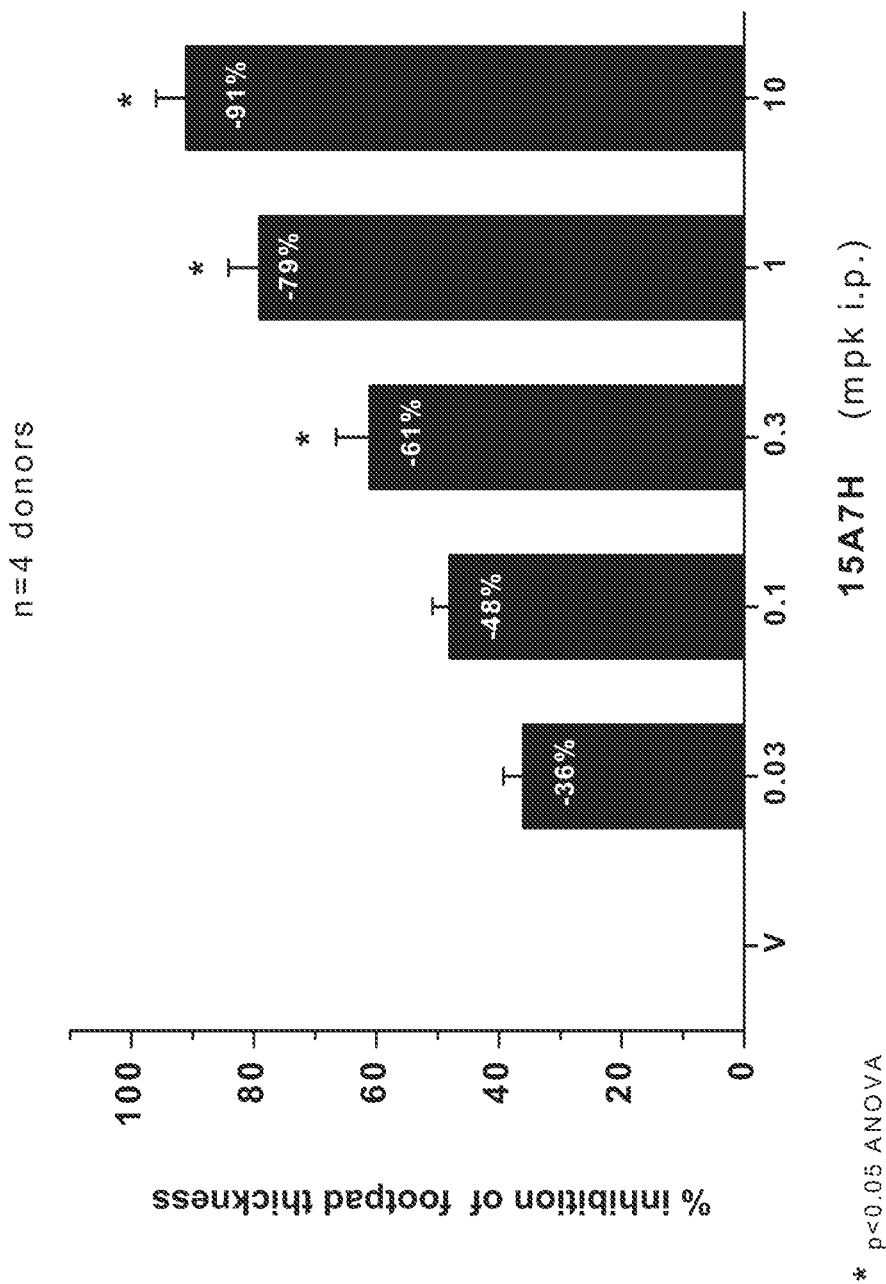

FIG. 3 depicts pooled dose response of 15A7H antibody in trans-vivo DTH in 4 donor PBMCs. The pooled mean±SEM of 4 donors after treatment with 0.03, 0.1, 0.3, 1 and 10 mg/kg antibody, or vehicle. pbmc: PBMC only, V: vehicle, 0.03, 0.1, 0.3,1 and 10 mg/kg of 15A7H antibody. Percent inhibitions of foot pad thickness in response to 0.03, 0.1, 0.3, 1, and 10 mg/kg of 15A7H antibody treatment.

Figure 4:
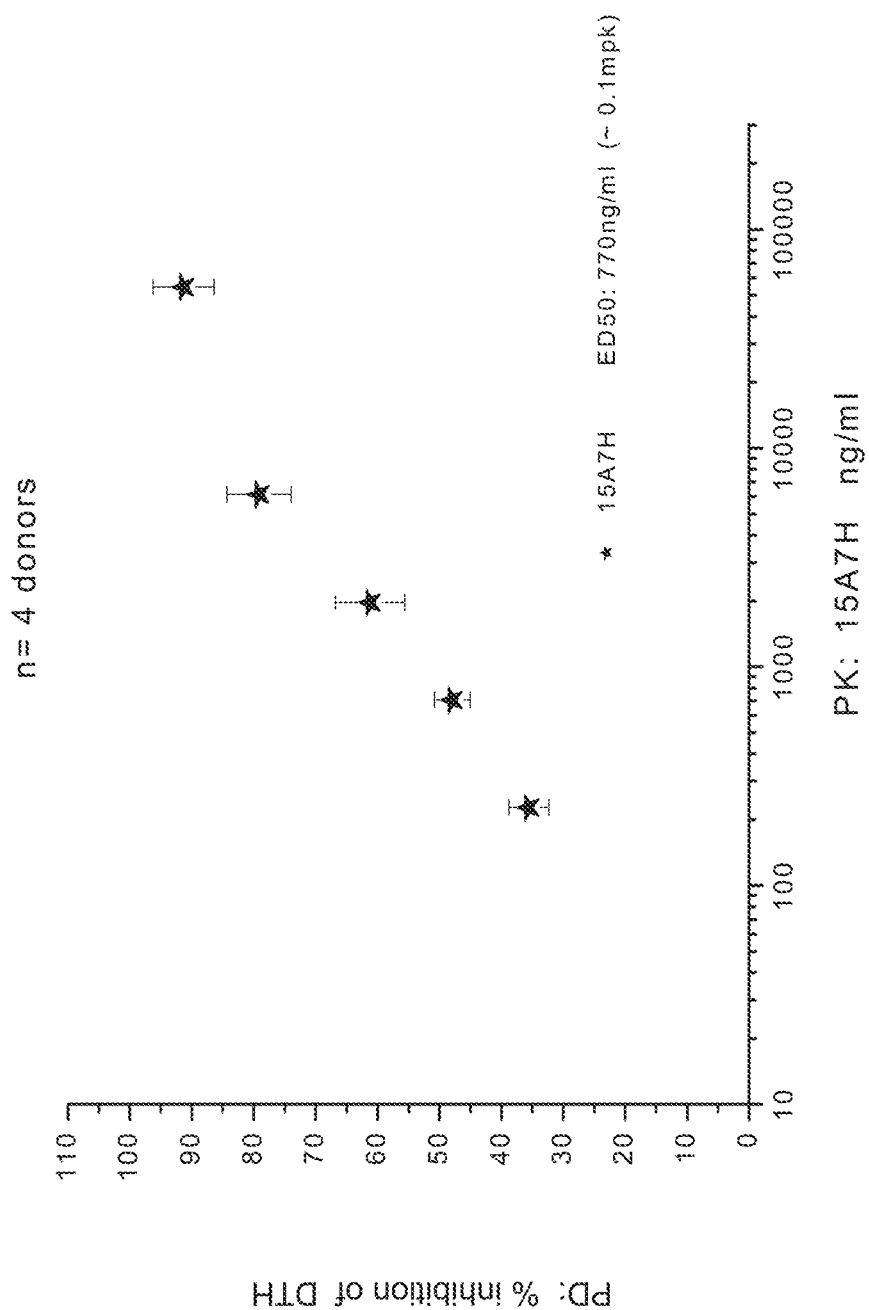

FIG. 4 depicts twenty four hour plasma concentrations of 15A7H antibody in C57BL/6 mice following a single intraperitoneal injection. Pooled plasma levels of the 2 antibodies (mean±SEM, n=4) in the experimental animals are plotted against their % inhibition of footpad thickness in the transvivo DTH assay.

Figure 5:
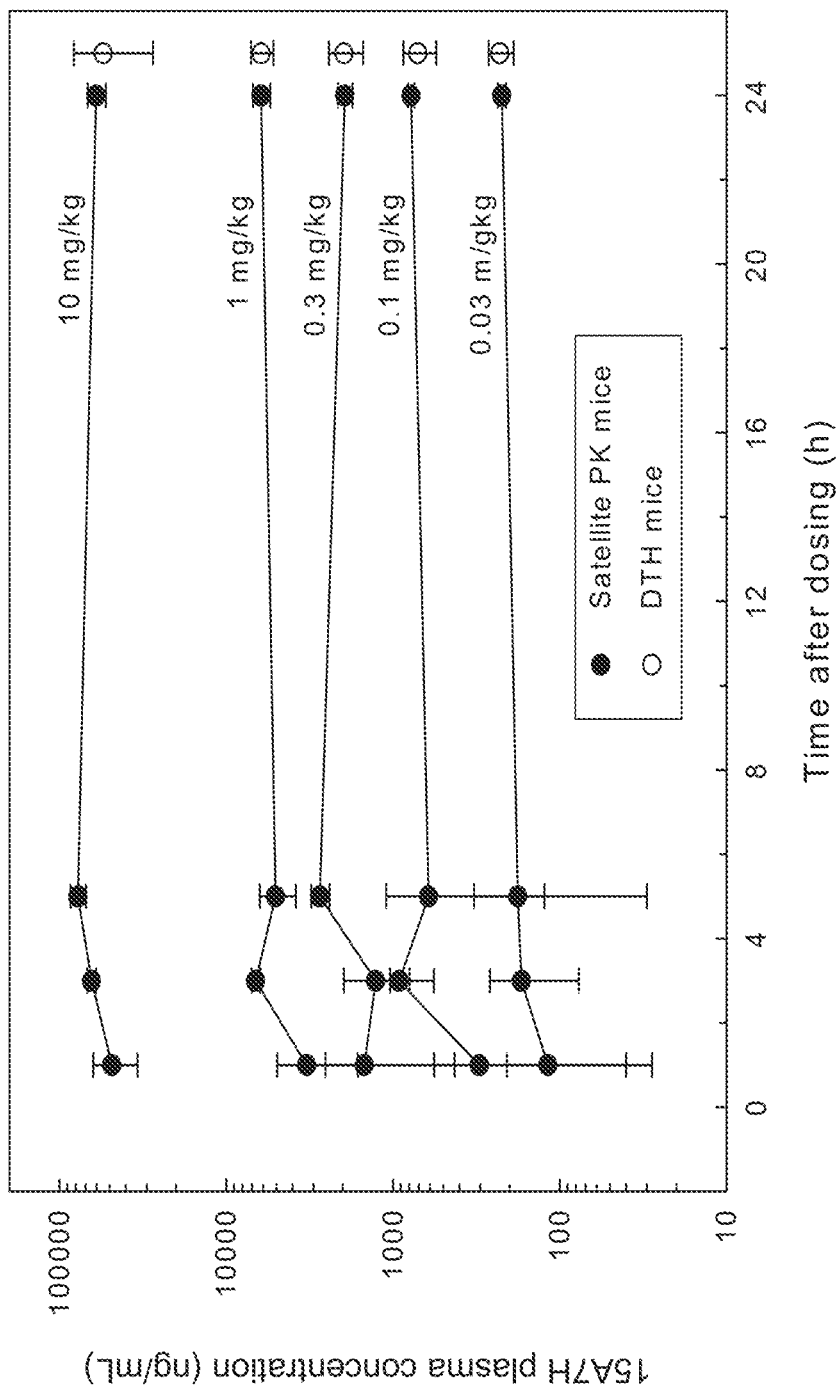

FIG. 5 depicts 15A7H plasma concentrations versus time in C57BL/6 mice. Four satellite mice were dosed i.p. with 0.03, 0.1, 0.3, 1, and 10 mg/kg of 15A7H antibody. Blood samples were collected at 1, 3, 5 and 24 hrs.

Figure 6:
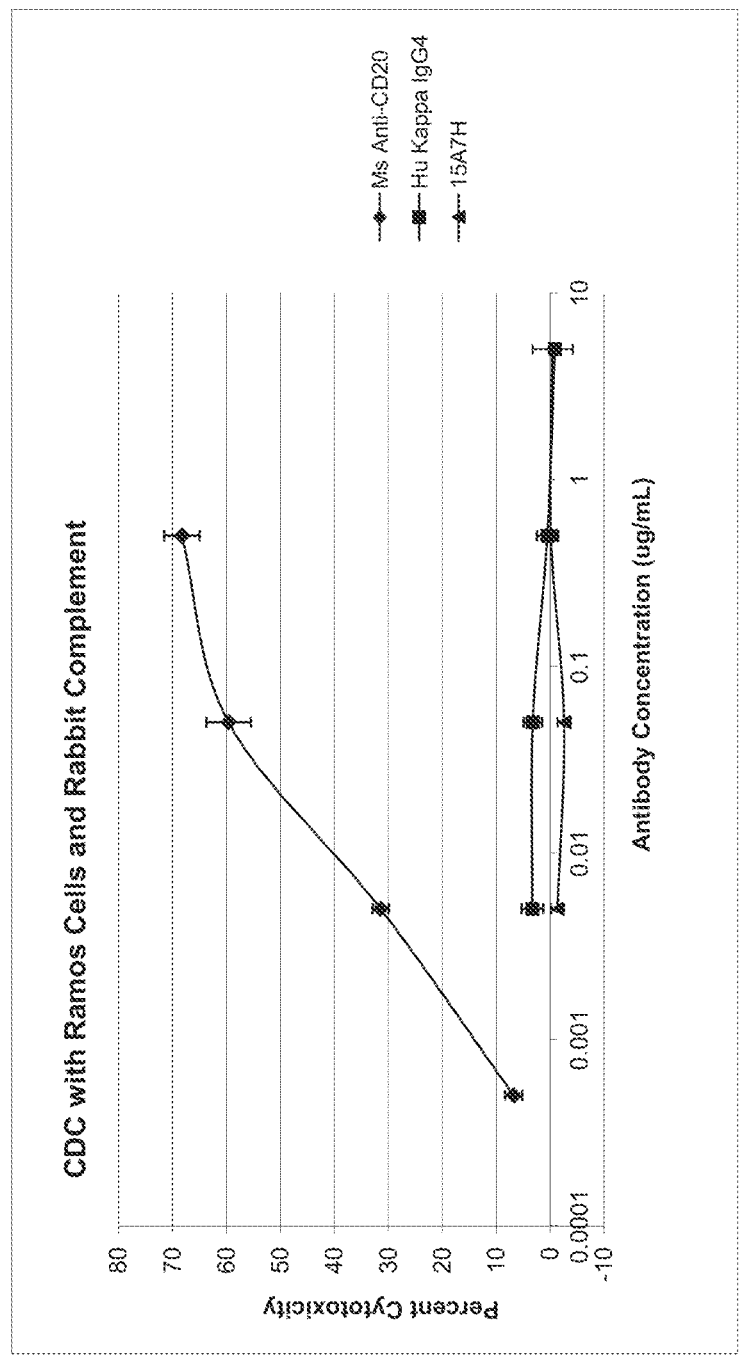

FIG. 6 depicts CDC activity of 15A7H and control antibodies, which were tested at different concentrations (5, 0.5, 0.05, 0.005 and 0.0005 µg/ml).

FIG. 7A depicts the heavy chain amino acid sequence of antibody 15A7H (SEQ ID NO:2). The variable heavy chain region (SEQ ID NO:4) is in bold. The CDRs (CDR1 (SEQ ID NO:8), CDR2 (SEQ ID NO:9), and CDR3 (SEQ ID NO:10)) are boxed. The framework regions (FR1 (SEQ ID NO:17), FR2 (SEQ ID NO:18), FR3 (SEQ ID NO:19), and FR4 (SEQ ID NO:20)) are also indicated. The constant region is indicated. The hinge region amino acid sequence (SEQ ID NO:12) is boxed. The substituted proline at amino acid position 228 in the hinge region is italicized.

FIG. 7B depicts the light chain amino acid sequence of antibody 15A7H (SEQ ID NO:1). The variable light chain region (SEQ ID NO:3) is in bold. The CDRs (CDR1 (SEQ ID NO:5), CDR2 (SEQ ID NO:6), and CDR3 (SEQ ID NO:7)) are boxed. The framework regions (FR1 (SEQ ID NO:13), FR2 (SEQ ID NO:14), FR3 (SEQ ID NO:15), and FR4 (SEQ ID NO:16)) are also indicated. The constant region is indicated.

TABLE 1

List of SEQ ID NOs and their corresponding sequences

| SEQ ID NO. | Corresponding Sequence |
| --- | --- |
| SEQ ID NO: 1 | 15A7H Light Chain amino acid sequence |
| SEQ ID NO: 2 | 15A7H Heavy Chain amino acid sequence |
| SEQ ID NO: 3 | 15A7H Variable Light Chain Region (VL) amino acid sequence |
| SEQ ID NO: 4 | 15A7H Variable Heavy Chain Region (VH) amino acid sequence |
| SEQ ID NO: 5 | 15A7H VL CDR1 amino acid sequence |
| SEQ ID NO: 6 | 15A7H VL CDR2 amino acid sequence |
| SEQ ID NO: 7 | 15A7H VL CDR3 amino acid sequence |
| SEQ ID NO: 8 | 15A7H VH CDR1 amino acid sequence |
| SEQ ID NO: 9 | 15A7H VH CDR2 amino acid sequence |
| SEQ ID NO: 10 | 15A7H VH CDR3 amino acid sequence |
| SEQ ID NO: 11 | Full length human PSGL-1 amino acid sequence |
| SEQ ID NO: 12 | IgG4 hinge region amino acid sequence |
| SEQ ID NO: 13 | 15A7H VL FR1 |
| SEQ ID NO: 14 | 15A7H VL FR2 |
| SEQ ID NO: 15 | 15A7H VL FR3 |
| SEQ ID NO: 16 | 15A7H VL FR4 |
| SEQ ID NO: 17 | 15A7H VH FR1 |
| SEQ ID NO: 18 | 15A7H VH FR2 |
| SEQ ID NO: 19 | 15A7H VH FR3 |
| SEQ ID NO: 20 | 15A7H VH FR4 |
| SEQ ID NO: 21 | IgG4 wild-type hinge region amino acid sequence |

6. DETAILED DESCRIPTION

Provided herein are antibodies that specifically bind to PSGL-1. Also provided are isolated nucleic acids encoding such antibodies. Further provided are vectors and host cells comprising nucleic acids encoding such antibodies or antigen-binding fragments thereof. Also provided are methods of making such antibodies, cells, e.g. CHO cells, antibodies produced by such cells and purification of produced antibodies. Also provided herein is a method of treating and/or preventing a disorder or disease described herein (e.g., an inflammatory condition) comprising administering an antibody or an antibody derived antigen-binding fragment described herein that immunospecifically binds to PSGL-1. In a specific embodiment, the antibody is the IgG4 monoclonal antibody 15A7H described in Examples 1-4, infra.

6.1 Antibodies

Provided herein are monoclonal antibodies that immunospecifically bind to human P-selectin glycoprotein ligand-1 ("PSGL-1"). In a specific embodiment, provided herein is a monoclonal antibody which immunospecifically binds to human PSGL-1 comprising: (i) a variable light ("VL") chain region comprising the amino acid sequence of SEQ ID NO: 3; (ii) a heavy chain comprising a variable heavy ("VH") chain region comprising the amino acid sequence of SEQ ID NO: 4; and (iii) a human IgG4 constant region which contains a Serine to Proline amino acid substitution at amino acid 228 of the heavy chain numbered according to the EU index. Non-limiting examples of human constant regions are described in the art, e.g., see Kabat et al. (1991) *Sequences of Proteins of Immunological Interest*, Fifth Edition, U.S. Department of Health and Human Services, NIH Publication No. 91-3242. Preferably, the antibody binds to PSGL-1 and selectively induces apoptosis of activated T cells (relative to other cells that express PSGL-1). In a specific embodiment, binding of the antibody to PSGL-1 does not interfere with the interaction of P-selectin with PSGL-1, a function associated with PSGL-1 and a requirement for efficient localization of activated T cells and neutrophils to target tissues.

In a specific embodiment, an antibody which immunospecifically binds to PSGL-1 is a full-length immunoglobulin G of class 4 (IgG4), and preferably comprises a heavy chain sequence of SEQ ID NO:2, and even more preferably comprises a heavy chain sequence of SEQ ID NO:2 and a light chain sequence of SEQ ID NO:1 (the latter being monoclonal antibody 15A7H).

Also provided herein are antigen-binding fragments of an antibody, comprising the variable region sequences SEQ ID NO:3 and SEQ ID NO:4 and at least a portion of a human heavy chain constant region containing the human IgG4 hinge region up through and including a Serine to Proline substitution at amino acid 228 of a human heavy chain numbered according to the EU index. In a specific embodiment, an antibody derived antigen-binding fragment herein is a F(ab')$_2$ fragment.

An antibody or an antibody derived antigen-binding fragment described herein is preferably isolated, most preferably purified.

As used herein and unless otherwise specified, the terms "immunospecifically binds," "immunospecifically recognizes," "specifically binds," and "specifically recognizes" are analogous terms in the context of antibodies and antibody derived antigen-binding fragments and are used interchangeably herein, and refer to the binding of an antibody or antibody derived antigen-binding fragment via its antigen combining site to its epitope, as would be understood by one skilled in the art. In one specific embodiment, an antibody or an antibody derived antigen-binding fragment that specifically binds to an antigen also can bind to other peptides or polypeptides, albeit generally with lower affinity as determined by, e.g., immunoassays, BIACORE™, KINEXA™ 3000 instrument (Sapidyne Instruments, Boise, ID), or other assays known in the art. In a specific embodiment, an antibody or an antibody derived antigen-binding fragment that immunospecifically binds to an antigen binds to the antigen with a $K_a$ that is at least 2 logs, 2.5 logs, 3 logs, 4 logs or greater than the $K_a$ when the antibody or the antibody derived antigen-binding fragment binds to another antigen. In another specific embodiment, an antibody or an antibody derived antigen-binding fragment that immunospecifically binds to an antigen do not cross react by binding with other proteins. In specific embodiments, an antibody or an antibody derived antigen-binding fragment described herein specifically binds to a native isoform or native variant of PSGL-1 (that is a naturally occurring isoform or variant of PSGL-1 in an animal that can be isolated from an animal, preferably a human). In particular embodiments, an antibody or an antibody derived antigen-binding fragment described herein immunospecifically binds to human PSGL-1 or a fragment thereof. In specific embodiments, an antibody or an antibody derived antigen-binding fragment described herein specifically binds to human PSGL-1 and/or cynomologous PSGL-1 or a fragment thereof.

The amino acid sequence of SEQ ID NO:11 depicts the full length human PSGL-1, GENBANK® accession number AAA74577.1, GI:902797. In specific embodiments, an antibody described herein immunospecifically binds to PSGL-1 as determined, e.g., by ELISA or other antigen-binding assay known in the art, or described herein.

In specific aspects, provided herein is an antibody that specifically binds human and/or cynomologous PSGL-1 and that is an immunoglobulin G (having a gamma-heavy region) of class 4 (an IgG4) that is a tetramer of two identical disulfide-bonded dimers, each comprising a heavy chain and a light chain. The antibody preferably comprises a heavy chain of SEQ ID NO:2. More preferably, the antibody comprises a heavy chain of SEQ ID NO:2 and a light chain of SEQ ID NO:1. With respect to the light chain, in a specific embodiment, the light chain of an antibody described herein is a kappa light chain.

In specific embodiments, an antibody described herein comprises a heavy chain comprising or consisting of the amino acid sequence of SEQ ID NO:2. In specific embodiments, an antibody described herein comprises a light chain comprising or consisting of the amino acid sequence of SEQ ID NO:1, and comprises a heavy chain comprising or consisting of the amino acid sequence of SEQ ID NO:2. In specific embodiments, an antibody described herein comprises a light chain comprising or consisting of the amino acid sequence of SEQ ID NO:1. In specific embodiments, an antibody described herein comprises a heavy chain comprising or consisting of the amino acid sequence of SEQ ID NO:2.

In a specific embodiment, the antibodies provided herein are IgG4 monoclonal antibodies that specifically bind to PSGL-1. IgG4 antibodies are known to undergo a process called Fab arm exchange, also known as IgG4 shuffling, in which increased susceptibility of native IgG4 hinge disulfide bonds to reduction allows the heavy chains to separate and randomly re-associate to produce a mixed population of IgG4 molecules with randomized heavy-chain and light-chain pairs (Aalberse et al., 1999. Int Arch Allergy Immunol 118:187-189; Labrijn, et al., 2009, Nat Biotechnol 27:767-771; Schuurman et al., 2001. Mol Immunol 38:1-8; van der Neut Kolfschoten et al., 2007. Science 317:1554-1557).

It has been demonstrated that a Serine to Proline mutation at position 241 using Kabat numbering (Kabat et al. 1991, *Sequences of Proteins of Immunological Interest*, Fifth Edition, U.S. Department of Health and Human Services, NIH Publication No. 91-3242) or at position 228 using the EU index (Edelman et al., 1969, Proc. Natl. Acad. Sci. USA, 63(1): 78-85) in the hinge region of human IgG4 results in considerable reduction of intra-chain disulfide bond formation, resulting in the reduction of IgG4 "half-antibody" molecules and reduced heterogeneity/shuffling of IgG4 molecules (Bloom et al. 1997, Protein Sci, 6:407-415; Angal et al., 1993, Molecular Immunology, 30(1): 105-108)). There are also published reports that this hinge mutation may decrease IgG4 shuffling and increase the half-life of the IgG4 molecules in vivo (Labrijn, et al., 2009, Nat Biotechnol 27:767-771; Stubenrauch, et al., 2010, Drug Metab Dispos 38:84-91). Van der Neut Kolfschoten et al., reported that the $C_H3$ domain of IgG4 and not the core hinge is predominantly involved in the Fab arm exchange reaction (see Van der Neut Kolfschoten et al, 2007, Science, 317: 1554-1557 ("Van der Neut Kolfschoten") at page 1555, col. 2). Van der Neut Kolfschaten reported that exchanging the $C_H3$ domain of IgG1 for the $C_H3$ domain of IgG4 activated Fab arm exchange for the IgG1, while exchanging the $C_H3$ domain of IgG4 abrogated Fab arm exchange for the IgG4 (see, p. 1555 and FIG. 2D).

In a specific embodiment, provided herein are IgG4 antibodies or antigen-binding fragments thereof, that specifically bind to PSGL-1, and that contain one or more amino acid substitutions in the IgG4 hinge region, wherein said antibody or antigen-binding fragment thereof retains specific binding to said PSGL-1 and wherein IgG4 shuffling is reduced relative to an antibody comprising an IgG4 hinge region not comprising said one or more amino acid substitutions. In a specific embodiment, the IgG4 hinge region only comprises a single amino acid substitution. An example of a "human IgG4 hinge region," is the region on the heavy chain of an IgG4 antibody between the $C_H1$ and $C_H2$ domains consisting of the amino acid sequence of SEQ ID NO:12, as set forth in Angal et al., 1993, Molecular Immunology, 30(1): 105-108.

In a specific embodiment, a reduction in IgG4 shuffling is determined by detecting of a lower amount of half antibody molecules or of arm exchange produced from an antibody described herein which contains one or more amino acid substitutions in the hinge region, as compared to the amount of half antibody molecules or of arm exchange produced from an IgG4 molecule containing an IgG4 hinge region not comprising said one or more amino acid substitutions. Any assay well-known in the art can be used to detect half antibody production and bispecific antibody molecules. See, e.g., Van der Neut Kolfschoten et al, 2007, Science, 317: 1554-1557, for examples of assays to detect production of bi-specific antibodies.

In a specific embodiment, provided herein are IgG4 monoclonal antibodies that specifically bind to PSGL-1, comprising a Serine to Proline amino acid substitution at amino acid position 228 of the heavy chain numbered according to the EU index.

In a specific embodiment, an antibody described herein comprises a light chain having the amino acid sequence of SEQ ID NO:1 and a heavy chain comprising a Proline at position 228 of the heavy chain numbered according to the EU index.

In a specific embodiment, a monoclonal antibody, which immunospecifically binds to human PSGL-1 comprises: (i) a light chain having the amino acid sequence of SEQ ID NO:1; and (ii) a heavy chain comprising a human IgG4 constant region containing one or more amino acid substitutions in the IgG4 hinge region, wherein said antibody retains specific binding to said PSGL-1 and wherein IgG4 shuffling is reduced relative to an antibody comprising an IgG4 hinge region not comprising said one or more amino acid substitutions.

In a specific embodiment, a monoclonal antibody, which immunospecifically binds to human PSGL-1 comprises (i) a light chain having the amino acid sequence of SEQ ID NO:1; and (ii) a heavy chain comprising a human IgG4 constant region comprising a Serine to Proline amino acid substitution at amino acid position 228 of the heavy chain numbered according to the EU index or position 241 according to the Kabat numbering system (Kabat et al. 1991, *Sequences of Proteins of Immunological Interest*, Fifth Edition, U.S. Department of Health and Human Services, NIH Publication No. 91-3242; and Edelman et al., 1969, Proc. Natl. Acad. Sci. USA, 63(1): 78-85).

In a specific embodiment, a monoclonal antibody, which immunospecifically binds to human PSGL-1 comprises: (i) a VL chain region comprising the amino acid sequence of SEQ ID NO:3; (ii) a VH chain region comprising the amino acid sequence of SEQ ID NO:4; and (iii) a human IgG4 constant region containing an IgG4 hinge region comprising one or more amino acid substitutions in the hinge region, wherein said antibody retains specific binding to PSGL-1 and wherein the IgG4 shuffling is reduced relative to an antibody comprising an IgG4 hinge region not comprising said one or more amino acid substitutions.

In a specific embodiment, a monoclonal antibody which immunospecifically binds to human PSGL-1 comprises: (i) a heavy chain comprising a VH chain region comprising the amino acid sequence of SEQ ID NO:4, and (ii) a human IgG4 heavy chain constant region comprising a Serine to Proline amino acid substitution at amino acid position 228 of the heavy chain numbered according to the EU index.

In a specific embodiment, a monoclonal antibody, which immunospecifically binds to human PSGL-1 comprises: (i) a VL chain region comprising the amino acid sequence of SEQ ID NO:3; (ii) a heavy chain comprising a VH chain region comprising the amino acid sequence of SEQ ID NO:4; and (iii) a human IgG4 heavy chain constant region comprising a Serine to Proline amino acid substitution at amino acid position 228 of the heavy chain numbered according to the EU index.

In certain embodiments, an IgG4 monoclonal antibody as described herein comprises the VH CDRs having the amino acid sequences described herein (e.g., see Table 3) and VL CDRs having the amino acid sequences described herein (e.g., see Table 2), wherein the antibody immunospecifically binds to PSGL-1 and has a hinge region mutation that reduces IgG4 shuffling (e.g., a Serine to Proline amino acid substitution at amino acid 228 of the heavy chain numbered according to the EU index). In a specific embodiment, the IgG4 monoclonal antibody immunospecifically binds PSGL-1 and comprises a heavy chain comprising (a) a VH chain region comprising SEQ ID NOs: 8, 9 and 10; and (b) a human IgG4 heavy chain constant region containing a Serine to Proline amino acid substitution at amino acid 228 of the heavy chain numbered according to the EU index. More preferably, the antibody further comprises a light chain comprising a VL chain region comprising SEQ ID NOs: 5, 6, and 7.

Table 2, below, presents the VL CDRs (in particular, VL CDR1, VL CDR2, and VL CDR3) of the amino acid sequence of 15A7H. Table 3, below, presents the VH CDRs (in particular, VH CDR1, VH CDR2, and VH CDR3) of the amino acid sequence of 15A7H. In specific embodiments, an antibody described herein which immunospecifically binds to human PSGL-1 (SEQ ID NO:11) comprises the VL CDR sequences in Table 2. In specific embodiments, an antibody described herein which immunospecifically binds to human PSGL-1 (SEQ ID NO:11), comprises the VH CDR sequences selected from those in Table 3.

TABLE 2

VL CDR Amino Acid Sequences

| Ab | VL CDR1 | VL CDR2 | VL CDR3 |
|---|---|---|---|
| 15A7H | RSSQSIVHNDGNTYFE (SEQ ID NO: 5) | KVSNRFS (SEQ ID NO: 6) | FQGSYVPLT (SEQ ID NO: 7) |

TABLE 3

VH CDR Amino Acid Sequences

| Ab | VH CDR1 | VH CDR2 | VH CDR3 |
|---|---|---|---|
| 15A7H | SFGMH (SEQ ID NO: 8) | YINGGSSTIFYANAVKG (SEQ ID NO: 9) | YASYGGGAMDY (SEQ ID NO: 10) |

In a specific embodiment, an antibody described herein immunospecifically binds to human PSGL-1 and comprises: (i) a variable light ("VL") chain region comprising a VL CDR1, VL CDR2, and VL CDR3 having the amino acid sequences of SEQ ID NO: 5, SEQ ID NO: 6, and SEQ ID NO: 7, respectively; (ii) a variable heavy ("VH") chain region comprising a VH CDR1, VH CDR2, and VH CDR3 having the amino acid sequences of SEQ ID NO: 8, SEQ ID NO: 9, and SEQ ID NO: 10, respectively; and (iii) a human IgG4 heavy chain constant region containing an IgG hinge region comprising one or more amino acid substitutions in the hinge region, wherein said antibody retains specific binding to said PSGL-1 and wherein IgG4 shuffling is reduced relative to an antibody comprising an IgG4 hinge region not comprising said one or more amino acid substitutions.

In a specific embodiment, an antibody described herein immunospecifically binds to human PSGL-1 and comprises: (i) a VL chain region comprising the amino acid sequence of SEQ ID NO: 3; (ii) a VH chain region comprising a VH CDR1, VH CDR2, and VH CDR3 having the amino acid sequences of SEQ ID NO: 8, SEQ ID NO: 9, and SEQ ID NO: 10, respectively; and (iii) a human IgG4 heavy chain constant region containing an IgG4 hinge region comprising one or more amino acid substitutions in the hinge region, wherein said antibody retains specific binding to said PSGL-1 and wherein IgG4 shuffling is reduced relative to an antibody comprising an IgG4 hinge region not comprising said one or more amino acid substitutions.

In a specific embodiment, an antibody described herein immunospecifically binds to human PSGL-1 and comprises: (i) a VL chain region comprising the amino acid sequence of SEQ ID NO: 3; (ii) a heavy chain comprising VH chain region comprising a VH CDR1, VH CDR2, and VH CDR3 having the amino acid sequences of SEQ ID NO: 8, SEQ ID NO: 9, and SEQ ID NO: 10, respectively; and (iii) a human IgG4 heavy chain constant region comprising a Serine to Proline amino acid substitution at amino acid position 228 of the heavy chain numbered according to the EU index.

In a specific embodiment, an antibody described herein immunospecifically binds to human PSGL-1 and comprises: (i) a VL chain region comprising a VL CDR1, VL CDR2, and VL CDR3 having the amino acid sequences of SEQ ID NO: 5, SEQ ID NO: 6, and SEQ ID NO: 7, respectively; (ii) a VH chain region comprising the amino acid sequence of SEQ ID NO: 4; and (iii) a human IgG4 heavy chain constant region containing an IgG4 hinge region comprising one or more amino acid substitutions in the hinge region, wherein said antibody retains specific binding to said PSGL-1 and wherein IgG4 shuffling is reduced relative to an antibody comprising an IgG4 hinge region not comprising said one or more amino acid substitutions.

In a specific embodiment, an antibody described herein immunospecifically binds to human PSGL-1 and comprises: (i) a VL chain region comprising a VL CDR1, VL CDR2, and VL CDR3 having the amino acid sequences of SEQ ID NO: 5, SEQ ID NO: 6, and SEQ ID NO: 7, respectively; (ii) a heavy chain comprising a VH chain region comprising the amino acid sequence of SEQ ID NO: 4; and (iii) a human IgG4 heavy chain constant region comprising a Serine to Proline amino acid substitution at amino acid position 228 of the heavy chain numbered according to the EU index.

In specific embodiments, an antibody described herein, which immunospecifically binds to PSGL-1, e.g., a human PSGL-1 polypeptide of SEQ ID NO:11, comprises framework regions (e.g., framework regions of the VL domain and VH domain). Non-limiting examples of human framework regions are described in the art, e.g., see Kabat et al. (1991) *Sequences of Proteins of Immunological Interest*, Fifth Edition, U.S. Department of Health and Human Services, NIH Publication No. 91-3242).

Table 4, below, presents the VL framework (FR) amino acid sequences (in particular, VL FR1, VL FR2, VL FR3, and VL FR4 sequences) of antibody 15A7H. Table 5, below, presents the VH FR amino acid sequences (in particular, VH FR1, VH FR2, VH FR3, and VH FR4 sequences) of antibody 15A7H.

TABLE 4

VL FR Amino Acid Sequences

| Ab | VL FR1 | VL FR2 | VL FR3 | VL FR4 |
|---|---|---|---|---|
| 15A7H | DIQMTQSPSSLSASVG DRVTITC (SEQ ID NO: 13) | WYQQKPGKAPKLL IY (SEQ ID NO: 14) | GVPSRFSGSGSGTHFTLTISS LQPEDFATYYC (SEQ ID NO: 15) | FGQGTKVEIKR (SEQ ID NO: 16) |

TABLE 5

VH FR Amino Acid Sequences

| Ab | VH FR1 | VH FR2 | VH FR3 | VH FR4 |
|---|---|---|---|---|
| 15A7H | EVQLVESGGGLVQPG GSLRLSCAASGFTFS (SEQ ID NO: 17) | WVRQAPGKGLEWVA (SEQ ID NO: 18) | RFTISRDNAKNTLYLQMNS LRAEDTAVYYCAR (SEQ ID NO: 19) | WGQGTLVTVSS (SEQ ID NO: 20) |

In certain embodiments, the above-described IgG4 antibodies having a mutation in the hinge region that reduces IgG4 shuffling comprise the VL FRs having the amino acid sequence described herein (see Table 4). In specific embodiments, an antibody described herein comprises a VL chain region comprising FR1, CDR1, FR2, CDR2, FR3, CDR3, and FR4 of Tables 1 and 3.

In certain embodiments, the above-described IgG4 antibodies having a mutation in the hinge region that reduces IgG4 shuffling comprise the VH FRs having the amino acid sequence described herein (see Table 5). In specific embodiments, an antibody comprises a VH chain region comprising FR1, CDR1, FR2, CDR2, FR3, CDR3, and FR4, of Tables 2 and 4.

In another specific embodiment, an IgG4 monoclonal antibody described herein comprises (i) a VL chain region comprising VL FR1, VL FR2, VL FR3, and VL FR4 having the amino acid sequences of SEQ ID NO: 13, 14, 15, and 16, respectively; and (ii) a VH chain region comprising VH FR1, VH FR2, VH FR3, and VH FR4 having the amino acid sequences of SEQ ID NO: 17, 18, 19, and 20, respectively, and has a mutation in the hinge region that reduces IgG4 shuffling. In a specific embodiment, an antibody described herein comprises a VL chain region comprising VL FR1, VL FR2, VL FR3, and VL FR4 having the amino acid sequences of SEQ ID NOs:13, 14, 15, and 16, respectively. In another specific embodiment, an antibody described herein comprises a VH chain region comprising VH FR1, VH FR2, VH FR3, and VH FR4 having the amino acid sequences of SEQ ID NOs:17, 18, 19, and 20, respectively.

In particular embodiments, the glycosylation of the constant region of antibodies described herein can be modified. For example, an aglycoslated constant region of an antibody can be made (i.e., the antibody constant region lacks glycosylation) or a constant region of an antibody comprising a mutation or substitution at one or more glycosylation sites to eliminate glycosylation at the one or more glycosylation sites can be made.

Glycosylation can occur via N-linked (or asparagine-linked) glycosylation or 0-linked glycosylation. N-linked glycosylation involves carbohydrate modification at the side-chain $NH_2$ group of an asparagine amino acid in a polypeptide. O-linked glycosylation involves carbohydrate modification at the hydroxyl group on the side chain of a serine, threonine, or hydroxylysine amino acid.

In certain embodiments, aglycosylated antibodies can be produced in bacterial cells which lack the necessary glycosylation machinery. Cells with altered glycosylation machinery have been described in the art and can be used as host cells in which to express recombinant antibodies described herein to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 03/035835; WO 99/54342.

In certain embodiments, one or more modifications can be made to the Fc region of an antibody described here, generally, to alter one or more functional properties of the antibody, such as serum half-life, complement fixation, Fc receptor binding, and/or antigen-dependent cellular cytotoxicity. These modifications are known in the art, and are described in for example, International Patent Application Publication No. WO 2008/153926 A2. Examples of such modifications include, but are not limited to: 1) altering the number of cysteine residues in the hinge region to facilitate assembly of the light and heavy chains or to increase or decrease the stability of the antibody; 2) mutating one or more amino acid in the CH2-CH3 domain interface region of the Fc-hinge fragment of an antibody to decrease the biological half life of the antibody; 3) replacing one or more amino acids selected from amino acid residues 234, 235, 236, 237, 297, 318, 320 and 322 according to the EU index of Kabat with a different amino acid residue such that the antibody has an altered affinity for an effector ligand but retains the antigen-binding ability of the parent antibody; and/or 4) modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439 according to the EU Index of Kabat to increase the ability of the antibody to mediate antibody dependent cellular cytotoxicity (ADCC) and/or to increase the affinity of the antibody for an Fcγ receptor. Provided herein are antibodies and antibody derived antigen-binding fragments that immunospecifically bind to PSGL-1 and that can modulate PSGL-1 activity. In certain embodiments, an antibody and antibody derived antigen-binding fragment provided herein immunospecifically binds to PSGL-1 without inhibiting PSGL-1 binding to P-selectin, and induces apoptosis of activated T cells. PSGL-1 activity can relate to any activity of PSGL-1 known or described in the art, e.g., activation of T cells during an inflammatory response. PSGL-1 activity or PSGL-1 function are used interchangeably herein. In certain aspects, PSGL-1 activity is induced by PSGL-1 ligand (e.g., P-selectin) binding to PSGL-1.

In certain embodiments, an anti-PSGL-1 antibody or an antibody derived antigen-binding fragment described herein does not block or inhibit binding of P-selectin to PSGL-1.

In a specific embodiment, an antibody or an antibody derived antigen-binding fragment described herein reduces leukocyte recruitment during an inflammatory response.

In certain aspects, an antibody or an antibody derived antigen-binding fragment described herein reduces or inhibit survival of cells that express PSGL-1 and respond to PSGL-1 activity signaling (e.g., cells that proliferate in response to PSGL-1 ligand stimulation, PSGL-1 signaling or selectin binding), e.g., induces apoptosis in activated T cells. Cell survival assays are described in the art and can be readily carried out by one of skill in the art. For example, cell viability can be assessed by using trypan-blue staining or other cell death or viability markers known in the art (e.g., Annexin-1, propidium iodine (PI) or 7-AAD, see Gerber A, Bohne M, Rasch J, Struy H, Ansorge S, Gollnick H., 2000. Investigation of annexin V binding to lymphocytes after extracorporeal photoimmunotherapy as an early marker of apoptosis. Dermatology. 2000; 201(2):111-7, Coder, D. M. 2001. Assessment of Cell Viability. Current Protocols in Cytometry. 9.2.1-9.2.14, and Muppidi, J., Porter, M. and Siegel, R. M. 2004. Measurement of Apoptosis and Other Forms of Cell Death. Current Protocols in Immunology. 59:3.17.1-3.17.36.).

In specific embodiments, antibodies described herein specifically bind to PSGL-1 and inhibit (e.g., partially or completely inhibit) activated T cell survival as assessed by methods described herein or known to one of skill in the art (e.g., trypan blue exclusion assay, see Coder, D. M. 2001. Assessment of Cell Viability. Current Protocols in Cytometry. 9.2.1-9.2.14). In some embodiments, the term "inhibit" or "inhibition" means the reduction or prevention of activated T cell survival. Activated T cell survival can be reduced by about 10%, about 20%, about 30%, about 40%, about 50%, about 60%, about 70%, about 80%, about 90%, about 100%, about 125%, about 150% or more compared to a control (e.g., T cell survival in the absence of the antibodies described herein or in the presence of a non-specific antibody).

In certain aspects, an anti-PSGL-1 antibody described herein is capable of inducing apoptosis (i.e., programmed cell death) of activated T cells that express PSGL-1. Apoptosis assays are described in the art and can be readily carried out by one of skill in the art (see, e.g., Muppidi, J., Porter, M. and Siegel, R. M. 2004. Measurement of Apoptosis and Other Forms of Cell Death. Current Protocols in Immunology. 59:3.17.1-3.17.36). The term "induce" or "inducing" means initiation of or an increase of apoptosis above a control level. Apoptosis of activated T cells can be induced by about 10%, about 20%, about 30%, about 40%, about 50%, about 60%, about 70%, about 80%, about 90%, about 100%, about 125%, about 150% or more compared to a control (e.g. Apoptosis of activated T cells in the absence of the antibodies describe herein or in the presence of a non-specific antibody).

T cells and T cell lines which are appropriate for use in the assays described herein relating to PSGL-1 activity are readily available (e.g., ARR, DU.528, Jurkat, H-SB2, RPMI 8402, CML-T1, Karpas 45, KE-37/SKW-3, SUP-T1, SUP-T3, MOLT 3/4, P12-Ichikawa, PF-382, CCRF-CEM, HPB-ALL, K-T1, TALL-1, MOLT 16/17, TALL-104, DND-41, Loucy, MOLT 13, Peer/Be13, HUT 78/H9, HUT 102, MT-1, DEL, JB6, Karpas 299, SU-DHL1, 12H5, 3DO54.8, 3DO11.10, 8DO51.15, or 3DO18.3) or can be readily identified using methods known in the art (see, e.g., Thornton, A. M. 2003. Fractionation of T and B Cells Using Magnetic Beads. Current Protocols in Immunology. 55:3.5A.1-3.5A.11., Hathcock, K. 2001. T Cell Enrichment by Cytotoxic Elimination of B Cells and Accessory Cells. Current Protocols in Immunology. 00:3.3.1-3.3.5., Horgan, K., Shaw, S. and Boirivant, M. 2009. Immunomagnetic Purification of T Cell Subpopulations. Current Protocols in Immunology. 85:7.4.1-7.4.9., and Kanof, M. E. 2001. Purification of T Cell Subpopulations. Current Protocols in Immunology. 00:7.3.1-7.3.5). In particular embodiments, cells or cell lines for use in cell proliferation assays can express PSGL-1, endogenously or recombinantly. Cells or cell lines for use in cell viability assays can express PSGL-1, endogenously or recombinantly, and exert changes in cell viability in response to PSGL-1 ligand or anti-PSGL-1 antibody binding. Cells or cell lines for use in apoptosis assays can express PSGL-1, endogenously or recombinantly, and exert changes in apoptosis in response to PSGL-1 ligand or anti-PSGL-1 antibody binding. Preferably the cells or cell lines are human (e.g. ARR, DU.528, Jurkat, H-SB2, RPMI 8402, CML-T1, Karpas 45, KE-37/SKW-3, SUP-T1, SUP-T3, MOLT 3/4, P12-Ichikawa, PF-382, CCRF-CEM, HPB-ALL, K-T1, TALL-1, MOLT 16/17, TALL-104, DND-41, Loucy, MOLT 13, Peer/Bei3, HUT 78/H9, HUT 102, MT-1, DEL, JB6, Karpas 299, or SU-DHL1).

Methods for determining immunospecific binding of an antibody to its target antigen are readily available and described in the art. For example, the affinities and binding properties of an antibody for its target antigen, can be determined by a variety of in vitro assay methods (biochemical or immunological based assays) known in the art such as equilibrium methods (e.g., enzyme-linked immunoabsorbent assay (ELISA), or radioimmunoassay (RIA)), or kinetics (e.g., BIACORE™ analysis), and other methods such as indirect binding assays, competitive inhibition assays, fluorescence resonance energy transfer (FRET), immunoprecipitation, gel electrophoresis and chromatography (e.g., gel filtration). These and other methods can utilize a label on one or more of the components being examined and/or employ a variety of detection methods including but not limited to chromogenic, fluorescent, luminescent, or isotopic labels. In certain embodiments, use of labels is not necessary, e.g., BIACORE™ systems utilize the natural phenomenon of surface plasmon resonance (SPR) to deliver data in real time, without the use of labels.

In a specific embodiment, the antibodies described herein are isolated. In a specific embodiment, the antibodies described herein are purified. In a particular embodiment, an antibody described herein is a recombinant monoclonal antibody.

In a particular embodiment, provided herein is an antibody or antibody derived antigen-binding fragment which has been modified in a manner suitable for large scale manufacturing. This can involve cloning polynucleotide sequences encoding the necessary domains of an anti-PSGL-1 antibody, such as one or more CDRs or FRs, into a suitable expression vector which also contains polynucleotide sequences encoding suitable constant regions, so that an entire antibody is produced. The polynucleotide sequences provided by the expression vectors are nucleotide sequences which can be optimized to maximize antibody yield and stability for cell culture manufacturing conditions and purification processes.

6.2 Polynucleotides

In certain aspects, provided herein are polynucleotides comprising a nucleotide sequence encoding an antibody or an antibody derived antigen-binding fragment described herein that immunospecifically bind to a PSGL-1 antigen, and vectors comprising such polynucleotides for recombinant expression in host cells (e.g., microbial organisms, such as E. coli and mammalian cells, such as murine hybridoma cells, CHO cells, and 3T3 fibroblasts). Provided herein are polynucleotides comprising nucleotide sequences encoding any of the antibodies or antibody derived antigen-binding fragment thereof provided herein, as well as vectors comprising such polynucleotide sequences, e.g., expression vectors for their efficient expression in host cells, e.g., mammalian cells. In a specific embodiment, the polynucleotide comprising nucleotide sequences encoding any of the antibodies or antibody derived antigen-binding fragments described herein are isolated or purified.

In particular aspects, provided herein are polynucleotides comprising nucleotide sequences encoding antibodies or antibody derived antigen-binding fragments, which immunospecifically bind to PSGL-1 and comprises an amino acid sequence as described herein.

In specific embodiments, a polynucleotide described herein encodes a heavy chain having the amino acid sequence of SEQ ID NO: 2.

The polynucleotides can comprise nucleotide sequences encoding a heavy chain comprising the VH FRs and CDRs of antibodies described herein (see, e.g., Tables 2 and 4) and further comprising a mutation in the hinge region that reduces IgG4 shuffling.

Also provided herein are polynucleotides encoding an antibody heavy chain comprising SEQ ID NO: 2, which are optimized, e.g., by codon/RNA optimization, replacement with heterologous signal sequences, and elimination of mRNA instability elements. Also provided herein are polynucleotides encoding an antibody light chain comprising SEQ ID NO: 1, which are optimized, e.g., by codon/RNA optimization, replacement with heterologous signal sequences, and elimination of mRNA instability elements. Methods to generate optimized nucleic acids encoding an antibody or an antibody derived antigen-binding fragment for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of an anti-PSGL-1 antibody or an antigen-binding fragment thereof relative to the expression of an anti-PSGL-1 antibody encoded by polynucleotides that have not been optimized. Furthermore, the polynucleotide sequences can be designed to match the preferred codon usage in the host cell, e.g. E. coli codon usage or CHO codon usage.

An optimized polynucleotide sequence encoding an antibody or an antibody derived antigen-binding fragment described herein can hybridize to an unoptimized polynucleotide sequence encoding an antibody or an antibody derived antigen-binding fragment described herein. In specific embodiments, an optimized nucleotide sequence encoding an antibody or an antibody derived antigen-binding fragment described herein hybridizes under high stringency conditions to an unoptimized polynucleotide sequence encoding an antibody or an antibody derived antigen-binding fragment described herein. In a specific embodiment, an optimized nucleotide sequence encoding an antibody or an antibody derived antigen-binding fragment described herein hybridizes under high stringency, intermediate or lower stringency hybridization conditions to an unoptimized nucleotide sequence encoding an antibody or an antibody derived antigen-binding fragment described herein. Information regarding hybridization conditions have been described, see, e.g., U.S. Patent Application Publication No. US 2005/0048549 (e.g., paragraphs 72-73), which is incorporated herein by reference in its entirety.

The polynucleotides can be obtained, and the nucleotide sequence of the polynucleotides determined, by any method known in the art. Nucleotide sequences encoding antibodies or antibody derived antigen-binding fragments described herein, and modified versions of these antibodies or antibody derived antigen-binding fragments can be determined using methods well known in the art, i.e., nucleotide codons known to encode particular amino acids are assembled in such a way to generate a nucleic acid that encodes the antibody or the antibody derived antigen-binding fragment. Such a polynucleotide encoding the antibody can be assembled from chemically synthesized oligonucleotides (e.g., as described in Kutmeier et al., 1994, BioTechniques 17:242), which, for example, involves the synthesis of overlapping oligonucleotides containing portions of the sequence encoding the antibody or the antibody derived antigen-binding fragment, annealing and ligating of those oligonucleotides, and then amplification of the ligated oligonucleotides by PCR. Various methods to generate synthetic genes from oligonucleotides are known in the art.

Alternatively, a polynucleotide encoding an antibody or an antibody derived antigen-binding fragment described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from cells producing the antibody of interest, e.g. hybridoma cells. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies. The constant chain is usually kappa or lambda for the antibody light chain, for the antibody heavy chain it can be, without limitation, any IgG isotype (e.g. human IgG1, IgG2, IgG3 or IgG4) or other immunoglobulins, including allelic variants.

If a clone containing a nucleic acid encoding a particular antibody is not available, but the sequence of the antibody molecule is known, a nucleic acid encoding the immunoglobulin can be chemically synthesized and cloned into replicable cloning vectors using any method well known in the art.

DNA encoding antibodies or antibody derived antigen-binding fragments described herein can be readily isolated and sequenced using conventional procedures (e.g., by using oligonucleotide probes that are capable of binding specifically to nucleic acids encoding the heavy and light chains of the antibodies). Once isolated, the DNA can be placed into expression vectors, which are then transfected into prokaryotic or eukaryotic host cells such as *E. coli* cells, yeast (*Pichia, Saccharomyces*) simian COS cells, Chinese hamster ovary (CHO) cells, myeloma cells (NS0), insect or plant cells that do not otherwise produce immunoglobulin protein, to obtain the synthesis of antibodies or antibody derived antigen-binding fragments in the recombinant host cells.

6.3 Host Cells and Recombinant Expression of Antibodies

In certain aspects, provided herein are host cells recombinantly expressing the antibodies or antibody derived antigen-binding fragments described herein and related expression vectors. Provided herein are expression vectors comprising polynucleotides comprising nucleotide sequences encoding antibodies or antibody derived antigen-binding fragments described herein for recombinant expression in prokaryotic and eukaryotic host cells, preferably in mammalian cells. Also provided herein are host cells comprising such expression vectors for recombinantly expressing antibodies or antibody derived antigen-binding fragments described herein. In a particular aspect, provided herein are methods for producing an antibody or an antibody derived antigen-binding fragment described herein, comprising expressing such antibody or antibody derived antigen-binding fragment from a host cell.

Recombinant expression of an antibody or an antibody derived antigen-binding fragment described herein that immunospecifically binds to a PSGL-1 antigen involves construction of an expression vector containing a polynucleotide that encodes the antibody or the antibody derived antigen-binding fragment. Once the polynucleotide encoding an antibody or an antibody derived antigen-binding fragment described herein has been obtained, the vector for the production of the antibody or the antibody derived antigen-binding fragment can be produced by recombinant DNA technology using techniques well-known in the art. Thus, methods for preparing an antibody or an antibody derived antigen-binding fragment by expressing a polynucleotide containing an antibody or an antibody derived antigen-binding fragment encoding nucleotide sequence(s) are described herein. Methods which are well known to those skilled in the art can be used to construct expression vectors containing antibody coding sequences or antibody derived antigen-binding fragment coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody described herein, a heavy or light chain of an antibody, a heavy or light chain variable domain of an antibody, or an antibody derived antigen-binding fragment, operably linked to a promoter, in particular, a promoter providing for expression in a mammalian cell. Such vectors can include the nucleotide sequence encoding the constant region of the antibody molecule (see, e.g., International Publication Nos. WO 86/05807 and WO 89/01036; and U.S. Pat. No. 5,122,464) and the variable domain of the antibody can be cloned into such a vector for expression of the entire heavy, the entire light chain, or both the entire heavy and light chains. Expression vectors include plasmids, retroviruses, cosmids, EBV-derived episomes, artificial chromosomes and the like. The expression vector and expression control sequences are selected to be compatible with the host cell. The recombinant expression vector may also encode a signal peptide that facilitates secretion of the antibody chains from a host cell. The signal peptide may be an immunoglobulin signal peptide, a heterologous peptide from a non-immunoglobulin protein or an artificial peptide.

The expression vector is transferred to a host cell by conventional techniques known in the art (e.g. liposome-mediated transfection, polycation-mediated transfection, protoplast fusion, microinjections, calcium phosphate precipitation, electroporation, transfer by viral vectors) and the transfected cells are then cultured by conventional techniques to produce an antibody or an antibody derived antigen-binding fragment described herein. Thus, provided herein are host cells containing a polynucleotide encoding an antibody or an antibody derived antigen-binding fragment described herein, operably linked to a heterologous promoter. In certain embodiments for the expression of double-chained antibodies, vectors encoding both the heavy and light chains can be co-expressed in the host cell for expression of the entire immunoglobulin molecule, as detailed below. In certain embodiments, a host cell contains a vector comprising a polynucleotide encoding both the heavy chain and light chain of an antibody described herein, or antigen-binding fragment thereof. In specific embodiments, a host cell contains two different vectors, a first vector comprising a polynucleotide encoding a heavy chain of an antibody described herein, or a fragment thereof (e.g., an antigen-binding fragment thereof), and a second vector comprising a polynucleotide encoding a light chain of an antibody described herein, or a fragment thereof (e.g., an antigen-binding fragment thereof). In other embodiments, a first host cell comprises a first vector comprising a polynucleotide encoding a heavy chain of an antibody described herein, or a fragment thereof, and a second host cell comprises a second vector comprising a polynucleotide encoding a light chain of an antibody described herein.

A variety of host-expression vector systems can be utilized to express antibody molecules or antibody derived antigen-binding fragments described herein (see, e.g., U.S. Pat. Nos. 5,807,715 and 7,604,800). Such host-expression systems represent vehicles by which the coding sequences of interest can be produced and subsequently purified, but also represent cells which can, when transformed or transfected with the appropriate nucleotide coding sequences, express an antibody molecule or an antibody derived antigen-binding fragment described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences or antibody derived antigen-binding fragment coding sequences; yeast (e.g., *Saccharomyces, Pichia*) transformed with recombinant yeast expression vectors containing antibody coding sequences or antibody derived antigen-binding fragment coding sequences; insect cell systems infected with recombinant virus expression vectors (e.g., baculovirus) containing antibody coding sequences or antibody derived antigen-binding fragment coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences or antibody derived antigen-binding fragment coding sequences; or mammalian cell systems (e.g., COS, CHO, BHK, MDCK, HEK 293, NS0, PER.C6, VERO, CRL7O3O, HsS78Bst, HeLa, and NIH 3T3 cells) harboring recombinant expression constructs containing promoters and/or enhancers derived from the genome of mammalian cells (e.g., metallothionein promoter, immunoglobulin promoter, actin promoter) or from mammalian viruses (e.g., the adenovirus late promoter; the vaccinia virus 7.5K promoter, CMV, Simian Virus 40). Other regulatory elements for expression in eukaryotic cells are polyadenylation signals such as BGH polyA, SV40 late or early polyA. Alternatively, polyadenylation signals of immunoglobulin or other genes can be used. In another specific embodiment, eukaryotic cells, especially for the expression of an IgG4 monoclonal antibody described herein, are used for the expression of an antibody described herein or antigen-binding fragment thereof. For example, mammalian cells such as Chinese hamster ovary (CHO) cells, in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In certain embodiments, antibodies described herein are produced by CHO cells or NS0 cells. In a specific embodiment, the expression of nucleotide sequences encoding antibodies or antibody derived antigen-binding fragments described herein which immunospecifically bind to a PSGL-1 antigen is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody or an antibody derived antigen-binding fragment is to be produced, for the generation of pharmaceutical compositions of an antibody molecule or an antibody derived antigen-binding fragment, vectors which direct the expression of high levels of fusion protein products that are readily purified can be desirable.

In addition, a host cell strain can be chosen which modulates the expression of the inserted sequences, or modifies and processes the gene product in the specific fashion desired. Such modifications (e.g., glycosylation) and processing of protein products can be important for the function of the protein. Different host cells have characteristic and specific mechanisms for the post-translational processing and modification of proteins and gene products. Appropriate cell lines or host cells can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, COS, MDCK, HEK 293, NIH 3T3, W138, BT483, Hs578T, HTB2, BT2O and T47D, NS0 (a murine myeloma cell line that does not endogenously produce any immunoglobulin chains), CRL7O3O and HsS78Bst cells. In certain embodiments, antibodies or antibody derived antigen-binding fragments described herein are produced in mammalian cells, such as CHO cells.

For long-term, high-yield production of recombinant antibodies or antibody derived antigen-binding fragments, stable expression is preferred. For example, mammalian cell lines which stably express the antibody molecule or the antibody derived antigen-binding fragment can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in non-selective media, and then are switched to a selective media. The selectable marker in the recombinant plasmid confers resistance to the selection and allows cells to stably integrate the plasmid into their chromosomes. After single cell cloning cells are expanded into production cell lines. This method can advantageously be used to engineer cell lines which express the antibody molecule or the antibody derived antigen-binding fragment. Such engineered cell lines can be particularly useful in screening and evaluation of compositions that interact directly or indirectly with the antibody molecule.

A number of selection systems can be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-2 15); and hygro, which confers resistance to hygromycin (Santerre et al., 1984, Gene 30:147). Methods commonly known in the art of recombinant DNA technology can be routinely applied to select the desired recombinant clone, and such methods are described, for example, in Ausubel et al. (eds.), *Current Protocols in Molecular Biology*, John Wiley & Sons, N Y (1993); Kriegler, *Gene Transfer and Expression*, A Laboratory Manual, Stockton Press, N Y (1990); and in Chapters 12 and 13, Dracopoli et al. (eds.), *Current Protocols in Human Genetics*, John Wiley & Sons, N Y (1994); Colberre-Garapin et al., 1981, J. Mol. Biol. 150:1, which are incorporated by reference herein in their entireties.

The expression levels of an antibody molecule or an antibody derived antigen-binding fragment can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing antibody or antibody derived antigen-binding fragment is amplifiable, increase in the level of inhibitor present in culture of host cell will increase the number of copies of the marker gene.

Since the amplified region is associated with the antibody or antibody derived antigen-binding fragment gene, production of the antibody or the antibody derived antigen-binding fragment will also increase (Crouse et al., 1983, Mol. Cell. Biol. 3:257).

The host cell can be co-transfected with two or more expression vectors described herein, the first vector encoding a heavy chain derived polypeptide and the second vector encoding a light chain derived polypeptide. The two vectors can contain identical selectable or different selections markers which enable sufficient expression of heavy and light chain polypeptides. The host cells can be co-transfected with different amounts of the two or more expression vectors.

Alternatively, a single vector can be used which encodes, and is capable of expressing, both heavy and light chain polypeptides. The coding sequences for the heavy and light chains can comprise cDNA or genomic DNA. The expression vector can be monocistronic or multicistronic. For example, a bicistronic nucleic acid construct can comprise in the following order a promoter, a heavy chain of an antibody described herein), and a light chain of an antibody described herein. In such an expression vector, the transcription of both chains can be driven by the promoter, whereas the translation of the mRNA from the heavy chain can be by a cap-dependent scanning mechanism and the translation of the mRNA from the light chain can be by a cap-independent mechanism, e.g., by an IRES.

In some embodiments, the antibody molecules or antibody derived antigen-binding fragments are produced by culturing the host cells for a period of time sufficient to allow for high expression of the molecules in the host cells. In some embodiments the molecules are expressed in mammalian cells, for example in CHO cells in serum-free media or in chemically defined media. In some embodiments, the antibody molecules or antibody derived antigen-binding fragments are recovered from the culture medium as a secreted polypeptide or it can be recovered from the host cell lysates if for example expressed without a secretory signal.

Once an antibody molecule or antibody derived antigen-binding fragment described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, precipitation, filtration, reverse phase HPLC, or by any other standard technique for the purification of proteins to obtain substantially homogenous and biologically active preparations of the molecules. Further, the antibodies or antibody derived antigen-binding fragments described herein can be fused to heterologous polypeptide sequences to facilitate purification.

In specific embodiments, an antibody or an antibody derived antigen-binding fragment described herein is isolated or purified. For example, in a particular embodiment, a preparation of an antibody or an antibody derived antigen-binding fragment described herein is substantially free of cellular material, media components and/or chemical precursors. The language "substantially free of cellular material" includes preparations of an antibody or an antibody derived antigen-binding fragment in which the antibody or the antibody derived antigen-binding fragment is separated from cellular components of the cells from which it is isolated or recombinantly produced. When the antibody or antibody derived antigen-binding fragment is recombinantly produced, it is also generally substantially free of culture medium, i.e., culture medium represents less than about 20%, 10%, 2%, 1%, 0.5%, or 0.1% of the volume of the protein preparation. When the antibody or the antibody derived antigen-binding fragment is produced by chemical synthesis, it is generally substantially free of chemical precursors or other chemicals, i.e., it is separated from chemical precursors or other chemicals which are involved in the synthesis of the protein. Accordingly, such preparations of the antibody or the antibody derived antigen-binding fragment have less than about 30%, 20%, 10%, 5% (by dry weight) of chemical precursors or compounds other than the antibody of interest or the antibody derived antigen-binding fragment of interest.

6.4 Pharmaceutical Compositions

Provided herein are compositions, pharmaceutical compositions, comprising an antibody or an antibody derived antigen-binding fragment described herein. In particular aspects, compositions described herein can be for in vitro, in vivo, or ex vivo uses. In specific embodiments, provided herein is a pharmaceutical composition comprising an antibody or antibody derived antigen-binding fragment described herein and a pharmaceutically acceptable carrier or excipient.

Therapeutic compositions containing an antibody or an antibody derived antigen-binding fragment provided herein can be prepared for storage by mixing the antibody having the desired degree of purity with optional physiologically acceptable carriers, excipients or stabilizers (*Remington's Pharmaceutical Sciences* (1990) Mack Publishing Co., Easton, PA; *Remington: The Science and Practice of Pharmacy*, 21st ed. (2006) Lippincott Williams & Wilkins, Baltimore, MD), in the form of lyophilized formulations or aqueous solutions. Acceptable carriers, excipients, or stabilizers are nontoxic to recipients at the dosages and concentrations employed, and include buffers such as phosphate, citrate, sodium citrate dehydrate, and other organic acids; and/or non-ionic surfactants such as TWEEN™ PLURONICS™ or polyethylene glycol (PEG).

Compositions, such as those described herein, can also contain more than one active compound (for example, molecules, e.g., antibody or antibodies described herein) as necessary for the particular indication being treated. In certain embodiments, formulations comprise an antibody or an antibody derived antigen-binding fragment provided herein and one or more active compounds with complementary activities that do not adversely affect each other. Such molecules are suitably present in combination in amounts that are effective for the purpose intended. For example, an antibody or antibody derived antigen-binding fragment described herein can be combined with one or more other therapeutic agents. Such combined therapy can be administered to the patient serially or simultaneously or in sequence.

The compositions to be used for in vivo administration can be sterile. This is readily accomplished by filtration through, e.g., sterile filtration membranes.

In specific aspects, the pharmaceutical compositions provided herein contain therapeutically effective amounts of an antibody or an antibody derived antigen-binding fragment provided herein, and optionally one or more additional prophylactic or therapeutic agents, in a pharmaceutically acceptable carrier. Such pharmaceutical compositions are useful in the prevention and/or treatment of a disorder or disease described herein, such as psoriasis, or one or more of the symptoms thereof. The term "therapeutically effective amount" refers to the amount that is safe and sufficient to prevent or treat a disease. As used herein, the term "treat", "treated," "treating" or "treatment" is used herein to mean provide a beneficial or desired clinical result in a subject with a disease. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

Pharmaceutical carriers suitable for administration of an antibody or an antibody derived antigen-binding fragment provided herein include any such carriers known to those skilled in the art to be suitable for the particular mode of administration. In one embodiment, an antibody or an antibody derived antigen-binding fragment is formulated into suitable pharmaceutical preparations, such as sterile solutions or suspensions for parenteral administration.

In addition, an antibody or an antibody derived antigen-binding fragment described herein can be formulated as the sole pharmaceutically active ingredient in the composition or can be combined with other active ingredients (such as one or more other prophylactic or therapeutic agents).

In the compositions, an antibody or an antibody derived antigen-binding fragment provided herein is mixed with a suitable pharmaceutical carrier. The concentrations of the antibody or antibody derived antigen-binding fragment in the compositions can, for example, be effective for delivery of an amount, upon administration, that prevents and/or treats a disorder or disease described herein (e.g., an inflammatory disorder) or symptom thereof.

In one embodiment, the compositions are formulated for single dosage administration. To formulate a composition, the weight fraction of compound is dissolved, suspended, dispersed or otherwise mixed in a selected carrier at an effective concentration such that the disorder is relieved, treated or one or more symptoms are ameliorated.

In certain aspects, an antibody or an antibody derived antigen-binding fragment provided herein is included in the pharmaceutically acceptable carrier in an effective amount sufficient to exert a therapeutically useful effect in the absence of, or with minimal or negligible, undesirable side effects on the patient treated. A therapeutically effective concentration can be determined empirically by testing the compounds in in vitro and in vivo systems using routine methods and then extrapolated therefrom for dosages for humans.

The concentration of antibody or antibody derived antigen-binding fragment in the pharmaceutical composition will depend on, e.g., the physicochemical characteristics of the antibody or the antibody derived antigen-binding fragment, the dosage schedule, and amount administered as well as other factors known to those of skill in the art.

The pharmaceutical compositions, in another embodiment, provide a dosage of from about 0.001 mg to about 100 mg of antibody or antibody derived antigen-binding fragment per kilogram of body weight per day. Pharmaceutical dosage unit forms can be prepared to provide from about 0.001 mg to about 100 mg, and/or a combination of other optional essential ingredients per dosage unit form. In a specific embodiment, the antibody or antibody derived antigen-binding fragment is formulated at a concentration of 40 mg/mL.

The antibody or the antibody derived antigen-binding fragment can be administered at once, or can be divided into a number of smaller doses to be administered at intervals of time. It is understood that the precise dosage and duration of treatment is a function of the disease or disorder described herein being treated and can be determined empirically using known testing protocols or by extrapolation from in vivo or in vitro test data. It is to be noted that concentrations and dosage values can also vary with the severity of the disease or disorder to be alleviated. It is to be further understood that for any particular subject, specific dosage regimens can be adjusted over time according to the individual need and the professional judgment of the person administering or supervising the administration of the compositions.

The pharmaceutical compositions are provided for administration to humans and animals in unit dosage forms, such as sterile parenteral solutions or suspensions containing suitable quantities of an antibody or an antibody derived antigen-binding fragment describe herein. The antibody or the antibody derived antigen-binding fragment is, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the antibody or the antibody derived antigen-binding fragment sufficient to produce the desired therapeutic effect, in association with the required pharmaceutical carrier, vehicle or diluent. Examples of unit-dose forms include ampoules and syringes. Unit-dose forms can be administered in fractions or multiples thereof. A multiple-dose form is a plurality of identical unit-dosage forms packaged in a single container to be administered in segregated unit-dose form. Examples of multiple-dose forms include vials, or bottles of pints or gallons. Hence, multiple dose form is a multiple of unit-doses which are not segregated in packaging.

In certain embodiments, an antibody or an antibody derived antigen-binding fragment described herein are in a liquid pharmaceutical composition. Liquid pharmaceutically administrable compositions can, for example, be prepared by dissolving, dispersing, or otherwise mixing an antibody described herein in a carrier, such as, for example, water, saline, aqueous dextrose, glycerol, glycols, ethanol, and the like, to thereby form a solution or suspension. If desired, the pharmaceutical composition to be administered can also contain minor amounts of nontoxic auxiliary substances such as wetting agents, emulsifying agents, solubilizing agents, and pH buffering agents and the like.

Actual methods of preparing such dosage forms are known, or will be apparent, to those skilled in this art; for example, see, e.g., *Remington's Pharmaceutical Sciences* (1990) Mack Publishing Co., Easton, PA; *Remington: The Science and Practice of Pharmacy,* 21st ed. (2006) Lippincott Williams & Wilkins, Baltimore, MD.

Dosage forms or compositions containing antibody in the range of 0.005% to 99.9% with the balance made up from non-toxic carrier can be prepared. Methods for preparation of these compositions are known to those skilled in the art.

Parenteral administration, in one embodiment, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents. Other routes of administration may include, enteric administration, intracerebral administration, nasal administration, intraarterial administration, intracardiac administration, intraosseous infusion, intrathecal administration, intravenous infusion, subcutaneous implantation or injection, intramuslcular administration, intrarectal administration intravaginal administration, intragastrical administration, intratracheal administration, intrapulmonary administration and intraperitoneal administration.

Preparations for parenteral administration include sterile solutions ready for injection, sterile dry soluble products, such as lyophilized powders, ready to be combined with a solvent just prior to use, including sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), water, and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Pharmaceutical carriers also include ethyl alcohol, polyethylene glycol and propylene glycol for water miscible vehicles; and sodium hydroxide, hydrochloric acid, citric acid or lactic acid for pH adjustment.

Illustratively, intravenous or intraarterial infusion of a sterile aqueous solution containing an antibody is an effective mode of administration. Another embodiment is a sterile aqueous or oily solution or suspension containing an active material injected as necessary to produce the desired pharmacological effect.

In a specific embodiment, a pharmaceutical preparation comprises sodium citrate, sodium chloride, citric acid, polysorbate 80, and water. In a specific embodiment, a pharmaceutical preparation comprises sodium citrate, sodium chloride, and citric acid. In a specific embodiment, a pharmaceutical preparation comprises 9.1 mM sodium citrate, 150 mM sodium chloride, and 0.9 mM citric acid. In a specific embodiment, a pharmaceutical preparation comprises an antibody or conjugate described herein at a concentration of 0.267 mM. In a specific embodiment, a pharmaceutical preparation comprises 2.676 g/L sodium citrate, 8.766 g/L sodium chloride, 0.2 g/L polysorbate 80, and 0.189 g/L citric acid. In a specific embodiment, a pharmaceutical preparation comprises an antibody or an antibody derived antigen-binding fragment described herein at a concentration of 40 g/L. Preferably, the foregoing pharmaceutical preparations are at pH 6.0.

In other embodiments, the pharmaceutical compositions are lyophilized powders, which can be reconstituted for administration as solutions, emulsions and other mixtures. They can also be reconstituted and formulated as solids or gels.

The lyophilized powder is prepared by dissolving an antibody provided herein, in a suitable solvent. In some embodiments, the lyophilized powder is sterile. The solvent can contain an excipient which improves the stability or other pharmacological component of the powder or reconstituted solution, prepared from the powder. Excipients that can be used include, but are not limited to, dextrose, sorbital, fructose, corn syrup, xylitol, glycerin, glucose, sucrose or other suitable agent. The solvent can also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

6.5 Therapeutic Methods

Antibodies and antibody derived antigen-binding fragments described herein are useful for treating disorders and diseases associated with or caused (in whole or in part) by increased proliferation and/or numbers of activated T cells relative to the proliferation and/or numbers of activated T cells found in healthy individuals or individuals not having the particular disorder or disease. Such diseases and disorders are known to one skilled in the art or can be ascertained by one of skill in the art. In a specific embodiment, antibodies and antibody derived antigen-binding fragments described herein are useful for treating an inflammatory disease or disorder. In one embodiment, the inflammatory disease is an autoimmune disease. In a specific embodiment, the inflammatory disease or disorder is psoriasis, plaque psoriasis, psoriatic arthritis, rheumatoid arthritis, Crohn's disease, and ankylotic spondylitis.

Non-limiting examples of disorders and diseases that can be treated using the antibodies and antibody derived antigen-binding fragments described herein include psoriasis, Crohn's disease, ankylosing spondylitis, arthritis (including rheumatoid arthritis, juvenile rheumatoid arthritis, osteoarthritis, and psoriatic arthritis), diabetes mellitus, multiple sclerosis, encephalomyelitis, myasthenia gravis, systemic lupus erythematosis, autoimmune thyroiditis, dermatitis (including atopic dermatitis and eczematous dermatitis), Sjogren's Syndrome, aphthous ulcer, iritis, conjunctivitis, keratoconjunctivitis, type I diabetes, inflammatory bowel diseases, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, allergies such as atopic allergy, AIDS, and T cell neoplasms such as leukemias or lymphomas.

In addition, antibodies and antibody derived antigen-binding fragments are useful for preventing and/or treating certain disorders and diseases associated with or caused (in whole or in part) by increased proliferation and/or numbers of activated T cells relative to the proliferation and/or numbers of activated T cells found in healthy individuals or individuals not having the particular disorder or disease. Non-limiting examples of disorders and diseases that can be prevented and/or treated using the antibodies and antibody derived antigen-binding fragments described herein include graft-versus-host disease and cases of transplantation rejection (including transplantation rejection using allogeneic or xenogeneic tissues) such as bone marrow transplantation, liver transplantation, kidney transplant, or the transplantation of any organ or tissue.

Accordingly, provided herein are methods for preventing and treating diseases and disorders described herein using an antibody or antibody derived antigen-binding fragment described herein. In a specific embodiment, such methods comprise administering to a subject in need thereof a therapeutically effective amount of an antibody or an antibody derived antigen-binding fragment described herein. In specific embodiments, the antibody administered to treat a disorder or disease described herein is 15A7H.

In one embodiment, "treatment" or "treating" a disorder or disorder refers to an amelioration of a disease or disorder, or at least one discernible symptom thereof. In another embodiment, "treatment" or "treating" refers to an amelioration of at least one measurable physical parameter associated with a disease or disorder, not necessarily discernible by the subject. In yet another embodiment, "treatment" or "treating" refers to inhibiting the progression of a disease or disorder, either physically, e.g., stabilization of a discernible symptom, physiologically, e.g., stabilization of a physical parameter, or both.

In specific embodiments, the treatment methods described herein provide for the reduction or amelioration of the progression, severity, and/or duration of a disorder or disease described herein. In further specific embodiments, the treatment methods described herein reduce one or more symptoms of a disorder or disease described herein.

In a particular embodiment, a method for treating a disorder or disease described herein, can achieve at least one, two, three, four or more of the following effects due to administration of a therapeutically effective amount of an antibody or an antibody derived antigen-binding fragment described herein: (i) the reduction or amelioration of the severity of the disorder or disease and/or one or more symptoms associated therewith; (ii) a reduction in the duration of one or more symptoms associated with the disorder or disease; (iii) the prevention of the recurrence of the disorder or disease; (iv) the regression of the disorder or disease and/or one or more symptoms associated therewith; (v) a reduction in hospitalization of a subject; (vi) the reduction in hospitalization length; (vii) the increase in the survival of a subject; (viii) the inhibition of the progression of the disorder or disease and/or one or more symptoms associated therewith; (ix) the enhancement or improvement of the therapeutic effect of another therapy; (x) a reduction or elimination of the disorder or disease; (xi) a reduction in mortality; (xii) a decrease in hospitalization rate; (xiii) the prevention of the development or onset of one or more symptoms associated with the disorder or disease.

In one embodiment, "prevention" or "preventing" a disorder or disease refers to the completion or partial inhibition of the onset or development of the disorder or disease.

In a specific embodiment, the disease or disorder treated in accordance with the methods described herein is psoriasis. It is generally accepted that T lymphocytes play a key role in the pathogenesis of psoriasis. In a specific embodiment, a method for treating psoriasis comprises administering to a subject in need thereof a therapeutically effective amount of an antibody or an antibody derived antigen-binding fragment described herein. In another specific embodiment, a method for ameliorating or preventing one or more symptoms of psoriasis comprises administering to a subject in need thereof a therapeutically effective amount of an antibody or an antibody derived antigen-binding fragment described herein. Symptoms of psoriasis include, but are not limited to, red patches of skin covered with silvery scales, raised patches of skin, small scaling spots on skin, dry skin, cracked skin, including pustules, itching skin, thickened, pitted or ridged nail, swollen and stiff joints.

In another embodiment, the disease or disorder treated in accordance with the methods described herein is plaque psoriasis. Plaque psoriasis or psoriasis vulgaris is the most common form of psoriasis and is characterized by sharply demarcated, raised erythematous skin plaques covered by silvery scale. There is a predilection of the lesions to involve the extensor surfaces of the extremities, the lumbosacral area, and the scalp. The corresponding histopathological findings include significant inflammatory cellular infiltration of the dermis and epidermis, increased numbers of dilated vessels, and a substantial thickening of the epidermis with disordered differentiation of keratinocytes and hyperkeratosis. Approximately one third of patients with plaque psoriasis are categorized as having moderate or severe disease and are consequently candidates for therapy beyond just topical treatment.

In a specific embodiment, a method for treating plaque psoriasis comprises administering to a subject in need thereof a therapeutically effective amount of an antibody or an antibody derived antigen-binding fragment described herein. In another specific embodiment, a method for ameliorating or preventing one or more symptoms of plaque psoriasis comprises administering to a subject in need thereof a therapeutically effective amount of an antibody or an antibody derived antigen-binding fragment described herein. Symptoms of plaque psoriasis include, but are not limited to, red patches of skin covered with silvery scales, raised patches of skin, small scaling spots on skin, dry skin, cracked skin, including pustules, itching skin, thickened, pitted or ridged nail, swollen and stiff joints.

In another embodiment, the disorder treated in accordance with the methods described herein is chronic plaque psoriasis. In a specific embodiment, a method for treating chronic plaque psoriasis comprises administering to a subject in need thereof a therapeutically effective amount of an antibody or an antibody derived antigen-binding fragment described herein. In another specific embodiment, a method described herein is for ameliorating or preventing one or more symptoms of chronic plaque psoriasis comprises administering to a subject in need thereof a therapeutically effective amount of an antibody or an antibody derived antigen-binding fragment described herein. Symptoms of plaque chronic psoriasis include, but are not limited to, single or multiple raised reddened patches of skin, ranging from coin-sized to larger, on any part of the body, including but not limited to the knees, elbows, lumbosacral regions, scalp, and nails.

In another embodiment, the disorder treated in accordance with the methods described herein is guttate psoriasis. In another specific embodiment, a method for treating guttate psoriasis comprises administering to a subject in need thereof a therapeutically effective amount of an antibody or an antibody derived antigen-binding fragment described herein. In another specific embodiment, a method for preventing or ameliorating one or more symptoms of guttate psoriasis comprises administering to a subject in need thereof a therapeutically effective amount of an antibody or an antibody derived antigen-binding fragment described herein. Symptoms of guttate psoriasis include, but are not limited to, flares of water drop shaped scaly plaques on the skin, followed by an infection, such as a streptococcal throat infection.

In another embodiment, the disease or disorder treated in accordance with the methods described herein is inverse psoriasis. In a specific embodiment, a method for treating inverse psoriasis (also called intertriginous psoriasis and flexural psoriasis) comprises administering to a subject in need thereof a therapeutically effective amount of an antibody or an antibody derived antigen-binding fragment described herein. In another specific embodiment, a method for preventing or ameliorating one or more symptoms of inverse psoriasis comprises administering to a subject in need thereof a therapeutically effective amount of an antibody or an antibody derived antigen-binding fragment described herein. Symptoms of inverse psoriasis include, but are not limited to, smooth, usually moist areas of skin that are red and inflamed, unlike the scaling associated with plaque psoriasis, on one or more of the following body parts: armpits, groin, under the breasts, and in other skin folds around the genitals and buttocks.

In another embodiment, the disease or disorder treated in accordance with the methods described herein is pustular psoriasis. In a specific embodiment, a method for treating pustular psoriasis comprises administering to a subject in need thereof a therapeutically effective amount of an antibody or an antibody derived antigen-binding fragment described herein. In another specific embodiment, a method described herein for preventing or ameliorating one or more symptoms of pustular psoriasis comprises administering to a subject in need thereof a therapeutically effective amount of an antibody or an antibody derived antigen-binding fragment described herein. Symptoms of pustular psoriasis include, but are not limited to, pus-filled blisters that vary in size and location, but mostly on the hands and feet.

In another embodiment, the disease or disorder treated in accordance with the methods described herein is erythodermic psoriasis. In a specific embodiment, a method for treating erythodermic psoriasis comprises administering to a subject in need thereof a therapeutically effective amount of an antibody or an antibody derived antigen-binding fragment described herein. In another specific embodiment, a method described herein for preventing or ameliorating one or more symptoms of erythodermic psoriasis comprises administering to a subject in need thereof a therapeutically effective amount of an antibody or an antibody derived antigen-binding fragment described herein. Symptoms of erythodermic psoriasis include, but are not limited to, periodic, widespread, fiery redness of the skin and the shedding of scales in sheets, rather than smaller flakes. The reddening and shedding of the skin are often accompanied by severe itching and pain, heart rate increase, and fluctuating body temperature.

In another embodiment, the disease or disorder treated in accordance with the methods described herein is rheumatoid arthritis. In a specific embodiment, a method for treating rheumatoid arthritis comprises administering to a subject in need thereof a therapeutically effective amount of an antibody or an antibody derived antigen-binding fragment described herein. In another specific embodiment, a method described herein is for preventing or treating one or more symptoms of rheumatoid arthritis comprises administering to a subject in need thereof a therapeutically effective amount of an antibody or an antibody derived antigen-binding fragment described herein. Symptoms of rheumatoid arthritis, include, but are not limited to, fatigue, loss of appetite, low fever, swollen glands, weakness, joint pain in wrists, elbows, shoulders, hips, knees, ankles, toes, jaw, hands, feet, fingers, and/or neck, morning stiffness, chest pain when taking a breath (pleurisy), eye burning, itching, and discharge, nodules under the skin, numbness, tingling, or burning in the hands and feet.

In another embodiment, the disease or disorder treated in accordance with the methods described herein is Crohn's disease. In a specific embodiment, a method for treating Crohn's disease comprises administering to a subject in need thereof a therapeutically effective amount of an antibody or an antibody derived antigen-binding fragment described herein. In another specific embodiment, a method described herein is for preventing or ameliorating one or more symptoms of Crohn's disease comprises administering to a subject in need thereof a therapeutically effective amount of an antibody or an antibody derived antigen-binding fragment described herein. Symptoms of Crohn's disease, but are not limited to, crampy abdominal (belly area) pain, fever, fatigue, loss of appetite, pain with passing stool (tenesmus), persistent, watery diarrhea, unintentional weight loss, constipation, eye inflammation, fistulas (usually around the rectal area, may cause draining of pus, mucus, or stools), joint pain, liver inflammation, mouth ulcers, rectal bleeding and bloody stools, skin lumps or sores (ulcers), and swollen gums.

In another embodiment, the disease or disorder treated in accordance with the methods described herein is ankylosing spondylitis. In a specific embodiment, a method for treating ankylosing spondylitis comprises administering to a subject in need thereof a therapeutically effective amount of an antibody or an antibody derived antigen-binding fragment described herein. In another specific embodiment, a method for ameliorating or preventing one or more symptoms of ankylosing spondylitis comprises administering to a subject in need thereof a therapeutically effective amount of an antibody or an antibody derived antigen-binding fragment described herein. Symptoms of ankylosing spondylitis include, but are not limited to, frequent pain and stiffness in the lower back and buttocks, spine, and/or neck; and pain and tenderness spreading to the ribs, shoulder blades, hips, thighs and heels; inflammation of the eye (iridocyclitis and uveitis), causing redness, eye pain, vision loss, floaters and photophobia; fatigue; and nausea In another embodiment, the disease or disorder treated in accordance with the methods described herein is diabetes mellitus. In a specific embodiment, a method for treating diabetes mellitus comprises administering to a subject in need thereof a therapeutically effective amount of an antibody or an antibody derived antigen-binding fragment described herein. In another specific embodiment, a method for ameliorating or preventing one or more symptoms of diabetes mellitus comprises administering to a subject in need thereof a therapeutically effective amount of an antibody or an antibody derived antigen-binding fragment described herein. Symptoms of diabetes mellitus include, but are not limited to, loss of weight, polyuria (frequent urination), polydipsia (increased thirst), polyphagia (increased hunger), cardiovascular disease, diabetic retinopathy, diabetic neuropathy, hyperosmolar nonketotic state, and diabetic ketoacidosis.

In particular embodiments, an antibody or an antibody derived antigen-binding fragment described herein is administered to a patient who has previously received, or is currently receiving, one or more other therapies.

In particular embodiments, an antibody or an antibody derived antigen-binding fragment described herein is administered to a patient who has previously received, or is currently receiving, one or more other therapies. In other particular embodiments, an antibody or an antibody derived antigen-binding fragment described herein is administered to a patient who is, or is suspected of being, resistant or refractory to an anti-inflammatory therapy.

In certain aspects, provided herein are methods for killing T cells in an individual in need thereof, wherein said method comprises administering to said individual an effective amount of an antibody or an antibody derived antigen-binding fragment described herein. In certain aspects, provided herein are methods for inducing apoptosis of activated T cells in an individual in need thereof, wherein said method comprises administering to said individual an effective amount of an antibody or an antibody derived antigen-binding fragment described herein.

In certain embodiments, an antibody or an antibody derived antigen-binding fragment described herein or pharmaceutical composition thereof may be administered by any suitable method to a subject in need thereof. Non-limiting examples of administration methods include intravenous infusion, subcutaneous injection or implantation, intramuscularly, intrathecally, intraperitoneally, intrarectally, intravaginally, intranasally, intragastrically, intratracheally, or intrapulmonarily delivery and/or any other method of physical delivery described herein or known in the art. In one embodiment, an antibody or an antibody derived antigen-binding fragment or a pharmaceutical composition thereof is administered systemically (e.g., parenterally) to a subject in need thereof. In another embodiment, an antibody or a pharmaceutical composition thereof is administered locally (e.g., intratumorally) to a subject in need thereof. Each dose may or may not be administered by an identical route of administration. In some embodiments, an antibody or an antibody derived antigen-binding fragment described herein can be administered via multiple routes of administration simultaneously or subsequently to other doses of the same or a different an antibody described herein.

When a disease, or a symptom thereof, is being treated, administration of the antibody or the antibody derived antigen-binding fragment typically occurs after the onset of the disease or symptoms thereof. When a symptom of a disease are being prevented, administration of the antibody or the antibody derived antigen-binding fragment typically occurs before the onset of the symptoms.

The dosage and frequency of administration of an antibody or an antibody derived antigen-binding fragment described herein or a pharmaceutical composition thereof is administered in accordance with the methods for preventing and/or treating while minimizing side effects. The exact dosage of an antibody or an antibody derived antigen-binding fragment described herein to be administered to a particular subject or a pharmaceutical composition thereof can be determined by a practitioner, in light of factors related to the subject that requires treatment. Factors which can be taken into account include the severity of the disease state, general health of the subject, age, and weight of the subject, diet, time and frequency of administration, combination(s) with other therapeutic agents or drugs, reaction sensitivities, and tolerance/response to therapy. The dosage and frequency of administration of an antibody or an antibody derived antigen-binding fragment described herein or a pharmaceutical composition thereof can be adjusted over time to provide sufficient levels of the antibody or an antibody derived antigen-binding fragment, or to maintain the desired effect.

The precise dose to be employed in the formulation will also depend on the route of administration, and the seriousness of an inflammatory disorder or disease, and should be decided according to the judgment of the practitioner and each patient's circumstances.

Effective doses can be extrapolated from dose-response curves derived from in vitro or animal model test systems.

In one embodiment, the dosage of an antibody or an antibody derived antigen-binding fragment described herein that is administered to a patient to prevent and/or treat a disease or disorder described herein is typically 0.001 mg/kg to 100 mg/kg of the patient's body weight. In another embodiment, a suitable dosage of an antibody or antibody derived antigen-binding fragment that is therapeutically effective for the prevention and/or treatment of a disease or disorder described herein is in the range of 0.01 mg/kg to 100 mg/kg of a patient's body weight.

In specific embodiments, an "effective amount" of an antibody or an antibody derived antigen-binding fragment described herein refers to an amount of an antibody or an antibody derived antigen-binding fragment described herein which is sufficient to achieve at least one, two, three, four or more of the following effects: (i) the reduction or amelioration of the severity of a disease or disorder described herein and/or one or more symptoms associated therewith; (ii) the reduction in the duration of one or more symptoms associated with disorder or disease described herein; (iii) the prevention in the recurrence of a disease or disorder; (iv) the regression of a disease or disorder and/or one or more symptoms associated therewith; (v) the reduction in hospitalization of a subject; (vi) the reduction in hospitalization length; (vii) the increase in the survival of a subject; (viii) the inhibition of the progression of disease or disorder and/or one or more symptoms associated therewith; (ix) the enhancement or improvement of the therapeutic effect of another therapy; (x) a reduction or elimination in disease or disorder; (xi) a reduction in mortality; (xii) a decrease in hospitalization rate; (xiii) the prevention of the development or onset of one or more symptoms associated with a disease or disorder; and (xiv) improvement in the quality of life as assessed by methods well known in the art, e.g., questionnaires. In some embodiments, "effective amount" as used herein refers to the amount of an antibody described herein to achieve a specified result described in Section 6, infra. In certain embodiments, an effective amount of an antibody or an antibody derived antigen-binding fragment is from about 0.01 mg to about 1,000 mg.

In some embodiments, a single dose of an antibody or an antibody derived antigen-binding fragment described herein is administered one or more times to a patient to prevent and/or treat a disorder or disease described herein.

In particular embodiments, an antibody or an antibody derived antigen-binding fragment, or pharmaceutical composition thereof is administered to a subject in accordance with the methods for preventing and/or treating a disorder or disease presented herein in cycles, wherein the antibody or the antibody derived antigen-binding fragment, or pharmaceutical composition is administered for a period of time, followed by a period of rest (i.e., the antibody or the antibody derived antigen-binding fragment, or pharmaceutical composition is not administered for a period of time).

An antibody or an antibody derived antigen-binding fragment provided herein can be administered prior to, concurrently with, or subsequent to the administration of one or more additional therapies (e.g., agents) for use in preventing and/or treating disorder or disease described herein. The use of the term "in combination" does not restrict the order in which an antibody or an antibody derived antigen-binding fragment and one or more additional therapies are administered to a subject. In specific embodiments, the therapies can be administered serially or sequentially.

In another specific embodiment, an antibody or an antibody derived antigen-binding fragment described herein are used in combination with an amount of another therapy (such as, e.g., an anti-inflammatory agent) to prevent and/or treat a disease or disorder described herein. In a specific embodiment, such a combination therapies has synergistic effect. In other embodiments, such a combination has an additive effect.

In a specific embodiment, the antibody or the antibody derived antigen-binding fragment and additional therapy permits the use of lower dosages (e.g., sub-optimal doses) of the antibody or the antibody derived antigen-binding fragment and/or the additional therapy and/or less frequent administration of the antibody or the antibody derived antigen-binding fragment described herein or the additional therapy to a subject. In certain embodiments, the ability to utilize lower dosages of an antibody or an antibody derived antigen-binding fragment described herein and/or of an additional therapy and/or to administer an antibody or an antibody derived antigen-binding fragment, or said additional therapy less frequently reduces the toxicity associated with the administration of an antibody or an antibody derived antigen-binding fragment, or of said additional therapy, respectively, to a subject without reducing the efficacy of an antibody or of said additional therapy, respectively, in the prevention and/or treatment of a disorder or disease described herein. In some embodiments, the administration of an antibody or an antibody derived antigen-binding fragment described herein in combination with an additional therapy results in improved efficacy of the antibody or an antibody derived antigen-binding fragment described herein and/or of said additional therapy in preventing and/or treating a disorder or disease described herein. In some embodiments, the administration of an antibody or an antibody derived antigen-binding fragment described herein and one or more additional therapies avoids or reduces adverse or unwanted side effects associated with the use of any single therapy.

In a specific embodiment, a subject administered an antibody or an antibody derived antigen-binding fragment described herein is an animal (e.g., a cynomologous or a human subject). In a preferred embodiment, a subject administered an antibody or an antibody derived antigen-binding fragment described herein is a human. In a specific embodiment, a subject administered an antibody or antibody derived antigen-binding fragment exhibits one or more symptoms of a disease or disorder described herein.

6.6 Cell-Based Methods

Provided herein are methods for inducing or enhancing apoptosis in a cell expressing PSGL-1 comprising contacting the cell with an effective amount of an antibody described herein. In one embodiment, the cell is an immune cell. In a specific embodiment, the cell is a T cell. In a more specific embodiment, the cell is an activated T cell. Methods for detecting apoptosis are described in the art and can be readily carried out by one of skill in the art. In specific embodiments, a method for inducing or enhancing apoptosis of activated T cells expressing PSGL-1 comprises contacting the cells with an effective amount of an antibody described herein, wherein the effective amount is sufficient to induce or enhance apoptosis as assessed by methods known to one of skill in the art.

Provided herein are methods for reducing or inhibiting the survival of cells expressing PSGL-1 comprising contacting the cell with an effective amount of an antibody described herein. In one embodiment, the cell is an immune cell. In a specific embodiment, the cell is a T cell. In a more specific embodiment, the cell is an activated T cell. Cell survival assays are described in the art and can be readily carried out by one of skill in the art. For example, cell viability can be assessed by using trypan-blue staining or other cell death markers (e.g., Annexin-5 staining) or viability markers (e.g., propidium iodine or 7-AAD exclusion) known in the art. In specific embodiments, a method for reducing or inhibiting survival of activated T cells expressing PSGL-1 comprises contacting the cells with an effective amount of an antibody described herein, wherein the effective amount reduces or to inhibits survival of the cells as assessed by methods known to one of skill in the art (e.g., trypan blue exclusion assay or propidium iodine or 7-AAD exclusion).

6.7 Kits

Provided herein is a pharmaceutical pack or kit comprising one or more containers filled with one or more of the ingredients of the pharmaceutical compositions described herein, such as an antibody or an antibody derived antigen-binding fragment provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

In a specific embodiment, provided herein is a kit comprising a first container containing an antibody or an antibody derived antigen-binding fragment described herein. In a specific embodiment, a kit comprises a first container that is a vial containing said antibody or said antibody derived antigen-binding fragment as a lyophilized sterile powder under vacuum, and the kit further comprises a second container comprising a pharmaceutically acceptable fluid.

In a specific embodiment, provided herein is an injection device containing an antibody or an antibody derived antigen-binding fragment described herein. In a specific embodiment, the injection device the antibody in sterile solution. In a specific embodiment, an injection device provided herein is a syringe.

Also provided herein are kits that can be used in the above methods. In one embodiment, a kit comprises an antibody or an antibody derived antigen-binding fragment described herein, preferably a purified antibody, in one or more containers. In a specific embodiment, the kits described herein contain a substantially isolated PSGL-1 as a control. In another specific embodiment, the kits described herein further comprise a control antibody which does not react with PSGL-1. In another specific embodiment, the kits described herein contain one or more elements for detecting the binding of an antibody or an antibody derived antigen-binding fragment to PSGL-1 (e.g., the antibody or the antibody derived antigen-binding fragment can be conjugated to a detectable substrate such as a fluorescent compound, an enzymatic substrate, a radioactive compound or a luminescent compound, or a second antibody which recognizes the first antibody or antibody derived antigen-binding fragment can be conjugated to a detectable substrate). In specific embodiments, the kit can include a recombinantly produced or chemically synthesized PSGL-1. PSGL-1 provided in the kit can also be attached to a solid support. In a more specific embodiment, the detecting means of the above described kit includes a solid support to which PSGL-1 is attached. Such a kit can also include a non-attached reporter-labeled anti-human antibody. In this embodiment, binding of the antibody or the antibody derived antigen-binding fragment to PSGL-1 can be detected by binding of the said reporter-labeled antibody.

7. EXAMPLES

The examples in this section (i.e., section 6) are offered by way of illustration, and not by way of limitation.

7.1 Example 1: Generating Anti-PSGL-1 Monoclonal Antibodies

Antibody h15A7 contains the humanized 15A7 heavy and light chain variable regions described in International Application Pub. No. WO 2005/110475, published Nov. 24, 2005, which is incorporated herein by reference in its entirety. Antibody h15A7 is an IgG4 isotype antibody with a kappa-type light chain. A $Ser^{228} \rightarrow Pro^{228}$ mutation was introduced by PCR using mutagenic primers into the hinge region of h15A7. The resulting hinge mutant of h15A7 is called 15A7H herein. The remaining protein sequence of 15A7H is identical to h15A7. The amino acid sequence of 15A7H is shown in FIG. 7 A-B and depicted in SEQ ID NOs: 1 and 2. The antibody encoding gene sequences for the heavy and light chains were introduced into eukaryotic expression vectors derived from the vector pAD-CMV1 (described in EP 393 438).

15A7H was generated using the methods known in the art. Briefly, recombinant expression vectors encoding in addition to the heavy and the light chains for 15A7H also encode dihydrofolate reductase (DHFR) and neomycin phosphotransferase selection markers, respectively, were co-transfected into the suspension adapted CHO-DG44 host cell. The selection of stably transfected cells took place two days after the transfection in selective hypoxanthine/thymidine-free medium and addition of the antibiotic G418. Once cells were recovered from the initial selection, a DHFR-based gene amplification was induced by the addition of methotrexate. By single cell deposition a monoclonal production cell line using a CHO-DG44 host cell was developed for 15A7H. For the production of the 15A7H antibody, cells were expanded for inoculum for the production bioreactor. The production bioreactor was run in a fed batch mode for 8 to 14 days. To support the production of antibody and to prolong the cell culture production period, a nutrient feed medium was added during the production stage. The cell culture broth was harvested by centrifugation and dead-end filtration to efficiently remove cells, providing cell free culture fluid (CCF) for further purification of the product. After cell removal during harvest, the protein was purified through protein A affinity chromatography and anion and cation exchange chromatography. In addition, two robust virus clearance steps, a low pH viral inactivation step and a nanofiltration step for virus removal were included.

The purity of 15A7H was determined by a capillary gel electrophoresis method. Samples were denatured with SDS (sodium dodecyl sulphate) and separated based on size in a capillary filled with a gel buffer that acts as a sieving medium. In reduced samples, disulfide bonds are reduced with 2-mercaptoethanol, resulting in separate peaks for heavy and light chains of the antibody. In non-reduced samples, iodoacetamide, an alkylating agent is added to avoid any fragmentation induced by sample preparation and to ensure that the main IgG peak remains intact.

Samples were injected electrokinetically and the mobilized proteins were detected by UV-absorbance at 200 nm using an UV detector. For reduced samples, the time corrected area percents (TCA %) of the sum of heavy and light chain (% LC+HC) are reported. The reportable value for non-reduced samples is the TCA % of the IgG main peak.

Figure 1:
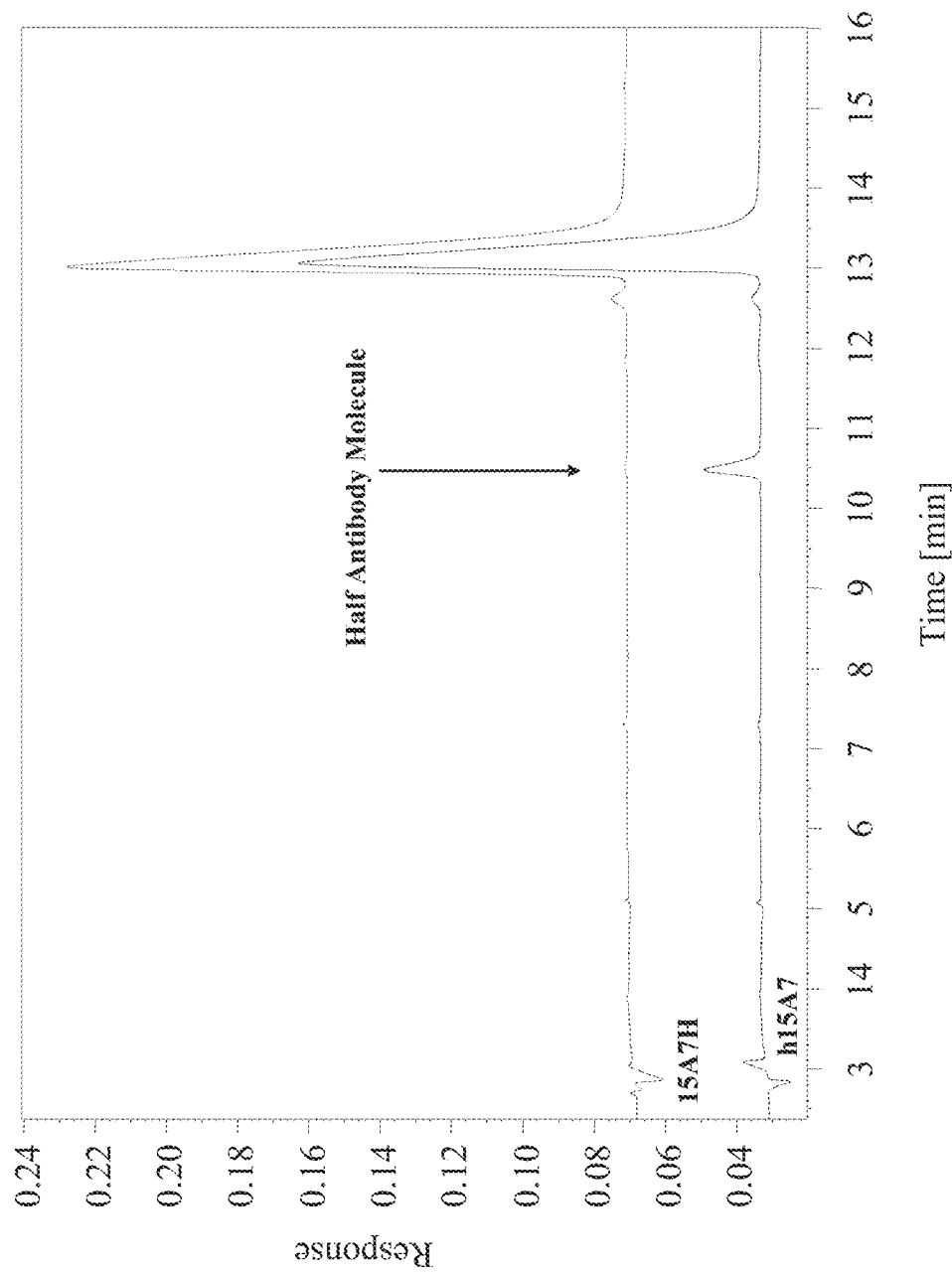
FIG. 1 depicts non-reducing capillary gel electrophoresis (CGE) for h15A7 and 15A7H. The arrow indicates the peak for the half antibody molecule.

A lower amount of half antibody molecules was detected by non-reducing capillary gel electrophoresis (CGE) (FIG. 1) indicating that the $Ser^{228} \rightarrow Pro^{228}$ mutation significantly lowered the formation of the intra-chain disulfide bond in the hinge region. The amount of half antibody molecules was reduced from ~8-10% for h15A7 to below 1% for 15A7H.

A formulation for 15A7H is shown in Table 6.

TABLE 6

| Formulation of 15A7H | | | |
|---|---|---|---|
| Components | Concentration [mmol/L] | Concentration [g/L] | Purpose of component |
| Sodium citrate dihydrate $C_6H_5Na_3O_7 \times 2\ H_2O$ | 9.1 | 2.676 | Buffer component |
| Sodium chloride | 150 | 8.766 | Tonicity agent |
| Polysorbate 80 | — | 0.2 | Stabilizer |
| Citric acid monohydrate $C_6H_8O_7 \times H_2O$ | 0.9 | 0.189 | Buffer component |
| 15A7H | 0.267 | 40 | Active ingredient |
| Water for injection (WFI) | — | add WFI to a final volume of 1.0 L | Solvent |

The pH of the formulation is 6.0.

7.2 Example 2: Binding of 15A7H Antibodies on Activated Primary Human T Cells 15A7H was examined for binding in primary activated human CD4+ T cells.

7.2.1. Materials and Methods

Cell Culture and T cell Activation Peripheral blood CD4+ T cells were cultured at 37° C. at 1×10⁶ in RPMI complete media and stimulated for 2 days with 20 ug/ml PHA-L (Sigma, Catalog #L2769) was added. Cells were incubated for an additional four to five days at 37° C. with 20 ng/ml IL-2 (R&D systems, Catalog #RD202-IL) to produce "activated CD4+ T cells".

Cell binding assay: Activated human CD4+ T cells were counted and plated at 1×10⁵ cells/100 µl in FACS buffer in a vbottom 96 well culture plate (BD FALCON™ Catalog #353263) and incubated on ice for 30 minutes.

An anti-lysozyme IgG4 isotype control, h15A7 and 15A7H were diluted to 90 ug/ml in FACS buffer in a round bottom dilution plate (FALCON™, Catalog #353077). Eleven 3 fold serial dilutions of antibody preparations were made for each antibody across the plate with a starting concentration of 30 ug/ml.

Duplicate cell samples were pelleted and resuspended in 100 µl of each antibody dilution for an initial starting concentration of 30 µg/ml. Cells were incubated on ice for 60 minutes. Cells were pelleted and washed with the wash buffer followed by addition of 100 μl of diluted secondary Goat F(ab)2 anti-human Ig's R-PE conjugate antibody. Secondary Goat F(ab')$_2$ anti-human Ig's R-PE conjugate antibody (BD Biosciences, Catalog #554655; stock at 1.05 mg/ml) was previously diluted 1:800 in FACS buffer Cells were incubated on ice for 30 minutes in dark then pelleted and washed a couple of times with the wash buffer. Cells were resuspended in 150 μl of wash buffer and fixed with addition of 50 μl of BD CYTOFIX/CYTOPERM™ fixation buffer (BD Biosciences, Catalog #554655).

Samples were analyzed on the BD FACSARRAY™ Bioanalyzer. About 5000 events were acquired using BD FACSARRAY™ flow cytometer for each cell sample with a "lymphocyte" gate set according to SSC and FSC and mean florescence that was determined for each sample.

Data Analysis: Anti-lysozyme IgG4, h15A7 and 15A7H antibody binding affinity to activated CD4+ T cells were determined by plotting antibody concentration versus mean fluorescence index (MFI) for each sample duplicate using XLfit (model: dose response one site, 205). EC50 values were determined for each binding curve.

7.2.2. Results

Figure 2:
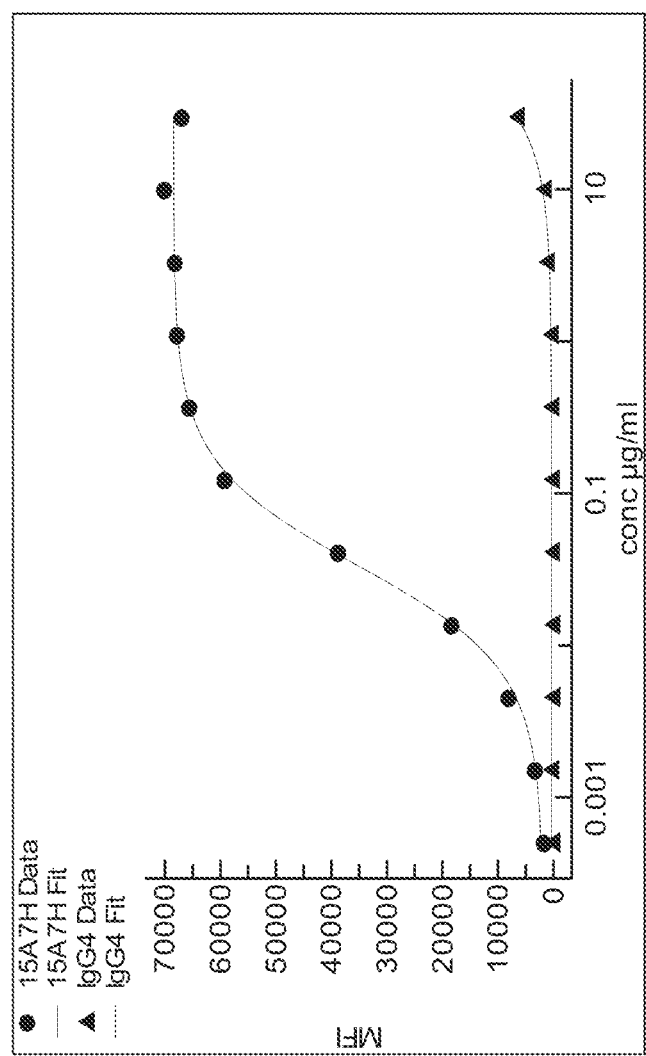
FIG. 2 depicts binding of 15A7H and control antibody to activated human CD4+ T-cells. EC50 values (nM) were derived using a one site 4-parameter fit model by plotting the mean fluorescence intensity (MFI) versus antibody concentration.

Binding to activated Human T cells: Using flow cytometry, the binding of 15A7H to activated human CD4+ T-cells was determined. FIG. 2 demonstrates that 15A7H bound with an EC50 of 0.22 nM.

Aggregate binding data from multiple donors demonstrates 15A7H bound to activated CD4+ T cells with a mean EC50 of 0.22+/−0.02. EC50 values from 4 donors were used to calculate Mean+/−SEM. Antibody h15A7 was tested under the same conditions and bound to activated CD4+ T cells with a mean EC50 of 0.27+/−0.05. Therefore, 15A7H and h15A7 demonstrated comparable binding to activated T cells (see Table 7).

TABLE 7

| Binding assay to activated CD4 T-cells. | |
|---|---|
| EC50 (nM) | Mean +/ − SEM |
| 15A7H | 0.22 +/ − 0.02 |
| h15A7 | 0.27 +/ − 0.05 |

7.3 Example 3: In-Vivo Activity of 15A7H in the Human Trans-Vivo Delayed-Type Hypersensitivity Mouse Model 15A7H was tested in the trans-vivo delayed-type hypersensitivity (DTH) model in female C57BL/6 mice. Doses of 0.03, 0.10, 0.3, 1 and 10 mg/kg of 15A7H were dosed i.p. in a formulation buffer. Antibody h15A7 was tested under the same conditions.

7.3.1. Materials and Methods

Trans Vivo Assay: Female C57BL/6 mice were purchased from Harlan Sprague Dawley, Inc. (Indianapolis, Indiana) at 6-8 weeks of age and used within four weeks of arrival. All mice were housed in a pathogen free environment, and treated according to NIH guidelines. All animal experiments were reviewed by and approved by the Institutional Animal Care and Use Committee (IACUC) and were conducted in conformity with the NIH guideline, "Guiding Principles for Research Involving Animals and Human Beings."

Blood was collected by venipuncture from normal human donors that were known to be good tetanus responders. One hundred ml whole blood was drawn into VACUTAINER® CPT™ tubes (Becton Dickinson, Franklin Lakes, NJ) and spun at 1800 RCF for 30 min. The buffy layer containing mononuclear cells and platelets was separated, washed three times, and resuspended in phosphate-buffered saline (PBS) and counted. Platelet contamination was minimized by multiple washes in PBS. No more than a 1:1 ratio of platelets to PBMCs was allowed. The cells were immediately injected into the mouse footpads.

Aluminium phosphate-adsorbed Tetanus toxoid (TT—TETGUARD™) was used at a concentration of 0.25 Lf per injection site (Lf unit is the flocculation value, the amount of toxoid which when mixed with one International Unit of antitoxin produces an optimal flocculating mixture).

7-10×10$^6$ PBMCs mixed with 0.25 Lf units of TT in a total volume of 50 μl, were injected into the hind footpads of mice. Footpad thickness was measured prior to injection and 24 hours post-injection, using a dial thickness gauge (Mitutoyo, Aurora, IL). Pre-injection thickness was subtracted from post-injection thickness at 24 hours to obtain the change in paw thickness. All measurements were made in inches.

Testing of 15A7H and h15A7: 15A7H and h15A7 (10 mg/ml stock) were dissolved in a vehicle containing 25 mM sodium citrate and 115 mM sodium chloride with 0.04% Tween 80, pH 5.97. Mice were injected i.p. with 0.2 ml of vehicle or 15A7H or h15A7 at 0.03, 0.1, 0.3, 1, and 10 mg/kg, one hour before footpad injections with PBMCs with or without TT. Each dose of 15A7H and h15A7 antibody was tested on PBMCs from four different donors and one mouse per treatment per donor was used. 15A7H and h15A7 treatment groups were compared to the vehicle treated group.

Statistics: All values are reported as the mean±SEM unless otherwise specified. The changes in footpad thickness in the drug treated group were compared to the vehicle treated group. Delta paw thicknesses from 4 individual donor experiments were pooled and mean±SEM was calculated. The percent inhibition of paw thickness was calculated as follows: 100×(Δ paw thickness$_{veh}$−Δ paw thickness$_{drug}$)/(Δ paw thickness$_{veh}$−Δpaw thickness$_{PBMC}$). Significance of inhibitory effects was tested using Kruskal-Wallis One Way Analysis of Variance (ANOVA) on Ranks. A p value of less than 0.05 was considered statistically significant.

Plasma levels of 15A7H and h15A7 in C57BL/6 mice: Plasma levels of 15A7H and h15A7 at 0.03, 0.1, 0.3, 1, and 10 mg/kg, 24 hours following intraperitoneal injection in female C57BL/6 mice were determined. Plasma samples were collected from trans-vivo DTH experimental animals upon termination of the experiment. Bioanalysis was performed on all samples.

Satellite Pharmacokinetic Study of 15A7H: Satellite female C57BL/6 mice receiving intraperitoneal doses of 15A7H (same dose levels as above) were used to collect data that are more intensive with respect to 15A7H plasma concentrations. These mice were not treated with human PBMCs or tetanus toxoid. Sampling times for these "PK" mice were 1, 3, 5, and 24 h after dosing. Each dose group of PK mice consisted of 6 mice. Within each dose group, a subgroup of 3 mice was used for sampling at 1 and 5 h, and another subgroup of 3 mice was used for sampling at 3 and 24 h.

Bioanalysis of h15A7 and 15A7H: A sandwich ELISA was used to quantitate concentrations of h15A7 or 15A7H in mouse plasma. Briefly, 96-well microtiter plates coated with PSGL-1 were used to bind either h15A7 or 15A7H in the diluted plasma sample. After washing, bound h15A7 or 15A7H was detected by a biotin-labeled monoclonal anti-human IgG4 antibody and enzyme (HRP)-labeled streptavidin. The amount of colored product formed during the substrate reaction was measured photometrically and increased with increasing concentration of h15A7 or 15A7H in the sample. The h15A7 or 15A7H concentration corresponding to the measured optical absorbance was calculated via data-fitting of the non-linear standard curve. The range of calibration samples was from 0.04 to 1.2 ng/mL. Samples were diluted at least 1:100. Thus, the lower limit of quantification of h15A7 or of 15A7H in whole plasma was 4 ng/mL. By using higher dilution factors the upper limit of quantification can be increased up to 2.4 mg/mL (1:2000000).

Due to slight differences of the reactivity of the h15A7 and 15A7H reference material in the ELISA, two calibration curves and two sets of quality controls were used. Samples from animals treated with h15A7 were analyzed versus the h15A7 calibration curve, and samples from animals treated with 15A7H were analyzed versus the 15A7H calibration curve.

7.3.2. Results

TRANS VIVO DTH: FIG. 3 shows pooled dose response of 15A7H antibody in trans vivo DTH in 4 donor PBMCs as shown by percent inhibition of DTH following treatment with 15A7H. When mice were dosed i.p. at −1 hour, with 0.03, 0.1, 0.3, 1, and 10 mg/kg, both h15A7 and 15A7H inhibited the trans vivo DTH in a dose dependent manner. Table 8 shows the dose response and percent inhibition of 15A7H and h15A7 in trans-vivo DTH. A single dose of 15A7H or h15A7 at 0.3 mg/kg and higher, showed significant inhibition of trans vivo DTH. The $ED_{50}$ for h15A7 and 15A7H in this assay was 0.09 and 0.1 mg/kg respectively, n=4 donors.

TABLE 8

Dose response and % inhibition of in trans-vivo DTH

| | | Mean | SEM | n |
|---|---|---|---|---|
| Delta (inches) | PBMC | 0.0005 | 0.0000 | 4 |
| | Vehicle | 0.0090 | 0.0010 | 4 |
| | h15A7 0.03 mpk | 0.0061 | 0.0007 | 4 |
| | h15A7 0.1 mpk | 0.0047 | 0.0008 | 4 |
| | h15A7 0.3 mpk | 0.0033 | 0.0006 | 4 |
| | h15A7 1 mpk | 0.0018 | 0.0003 | 4 |
| | h15A7 10 mpk | 0.0009 | 0.0001 | 4 |
| | 15A7H 0.03 mpk | 0.0060 | 0.0007 | 4 |
| | 15A7H 0.1 mpk | 0.0049 | 0.0006 | 4 |
| | 15A7H 0.3 mpk | 0.0040 | 0.0010 | 4 |
| | 15A7H 1 mpk | 0.0024 | 0.0006 | 4 |
| | 15A7H 10 mpk | 0.0012 | 0.0004 | 4 |
| % inhibition | Vehicle | 0.00 | 0.00 | 4 |
| | h15A7 0.03 mpk | 33.31 | 6.67 | 4 |
| | h15A7 0.1 mpk | 51.02 | 2.52 | 4 |
| | h15A7 0.3 mpk | 67.83 | 4.26 | 4 |
| | h15A7 1 mpk | 85.14 | 3.17 | 4 |
| | h15A7 10 mpk | 95.43 | 1.41 | 4 |
| | 15A7H 0.03 mpk | 35.56 | 3.25 | 4 |
| | 15A7H 0.1 mpk | 47.95 | 2.88 | 4 |
| | 15A7H 0.3 mpk | 61.20 | 5.62 | 4 |
| | 15A7H 1 mpk | 79.15 | 5.19 | 4 |
| | 15A7H 10 mpk | 91.32 | 4.94 | 4 |

COMPOUND PLASMA CONCENTRATIONS: The plasma concentrations of 15A7H for both satellite PK and DTH mice are summarized in FIG. 5. FIG. 4 shows 24 hour pooled plasma concentrations of 15A7H plotted against % inhibition of DTH. Note that the mean concentrations at 24 hours after dosing for the PK and DTH mice for a given dose level were very similar. This suggests that, although the PK and DTH mice were treated differently (only DTH mice received PBMCs and tetanus toxoid), the pharmacokinetics of 15A7H in the two cases were very similar. Plasma concentrations of both h15A7 and 15A7H fluctuated only within a fairly narrow range over the time course of the study (concentration measurements between 1 and 24 hr after dosing).

PK-PD: Table 9 and Table 10 show twenty four hour plasma concentrations (PK) of h15A7 and 15A7H antibodies and the corresponding percent inhibition of trans-vivo DTH (PD) at the same doses. FIG. 4 compares the PK-PD relationship of 15A7H in the trans-vivo DTH model. The $ED_{50}$ for h15A7 and 15A7H were calculated to be 687 and 770 ng/ml respectively, n=4 donors.

TABLE 9

PK-PD relationship in the trans-vivo DTH model.

| h15A7 dose mg/kg, i.p. | Mean | SEM | n |
|---|---|---|---|
| (A) Phamacokinetics (PK) ng/ml | | | |
| 0.03 | 111 | 12 | 4 |
| 0.1 | 618 | 64 | 4 |
| 0.3 | 2320 | 172 | 4 |
| 1 | 9355 | 642 | 4 |
| 10 | 67668 | 23686 | 4 |
| (B) Pharmacodynamics (PD) % inhibition | | | |
| 0.03 | 33 | 7 | 4 |
| 0.1 | 51 | 3 | 4 |
| 0.3 | 68 | 4 | 4 |
| 1 | 85 | 3 | 4 |
| 10 | 95 | 1 | 4 |

TABLE 10

PK-PD relationship in the trans-vivo DTH model.

| 15A7H dose mg/kg, i.p. | Mean | SEM | n |
|---|---|---|---|
| (A) Phamacokinetics (PK) ng/ml | | | |
| 0.03 | 228 | 20 | 4 |
| 0.1 | 708 | 79 | 4 |
| 0.3 | 1968 | 228 | 4 |
| 1 | 6163 | 469 | 4 |
| 10 | 54725 | 13612 | 4 |
| (B) Pharmacodynamics (PD) % inhibition | | | |
| 0.03 | 36 | 3 | 4 |
| 0.1 | 48 | 3 | 4 |
| 0.3 | 61 | 6 | 4 |
| 1 | 79 | 5 | 4 |
| 10 | 91 | 5 | 4 |

7.3.3. Conclusion

A single dose of 15A7H or h15A7 at 0.3 mg/kg and higher, showed significant percent inhibition of trans vivo DTH. The $ED_{50}$ for h15A7 and 15A7H in the trans-vivo DTH assay was 0.09 and 0.1 mg/kg, respectively. Plasma concentrations of both h15A7 and 15A7H fluctuated only within a fairly narrow range over the time course of the study.

7.4 Example 4: Assessment of Complement-Dependent Cytotoxicity (CDC)

In an effort to determine whether 15A7H has CDC activity, lactate dehydrogenase release assays were used to measure the CDC activity at various concentrations.

7.4.1. Materials and Methods

Ramos cells (obtained ATCC; cat #CRL-1596) were used as target cells and were cultivated in complete DMEM medium (Invitrogen, Carlsbad, CA; Catalog number 11995) with 0.5 mg/ml GENETICIN™ (Invitrogen, Carlsbad, CA; Catalog number 10131). Rabbit complement was used as the source of complement proteins (Accurate Chemical &Scientific Corp., Westbury, NY; catalog number: AIC4000-1). CEDARLANE™ Cytotoxicity medium was used as the assay media (Accurate Chemical &Scientific Corp., Westbury, NY; Catalog Number: CL95100).

CDC activity was determined by LDH release of target cells using Cytotoxicity Detection Kit$^{PLUS}$ (LDH) (Roche Applied Science, Indianapolis, IN; Catalog Number: 04 744 934 001). Mouse anti-human CD20 purified from 1F5 hybridoma (ATCC), Birmingham, AL; Catalog Number: 6140-01) was used to activate complement as a positive control antibody in the assay. Human IgG4κ(Sigma-Aldrich, St. Louis, MO; Catalog Number: 14639) was used as an isotype control. Samples and controls were set up as follows (All the samples have duplicates):

Samples: 100 µl standard rabbit complement (diluted 1:6 in assay media)+50 µl target cells (Ramos cells in assay media)+50 µl antibody dilutions Background control: 200 µl assay media Maximal release control: 50 µl target cells+100 µl standard rabbit complement+50 µl assay media Spontaneous release control: 50 µl target cells+100 µl standard rabbit complement+50 µl assay media The plate was incubated at 37° C. in a humid CO$_2$ incubator for 3 hrs. 30 min before the end of incubation (after 2.5 hrs incubation), 10 µl Lysis Solution (provided in the Cytotoxicity Detection Kit) was added to the maximal release control sample. At the end of the incubation, the plate was centrifuged at 200 g for 10 min at room temperature, and 100 µl of cell-free supernatants were transferred into corresponding wells of a 96-well flat-bottom plate for LDH detection. 100 µl of Reaction Mixture (provided in the Cytotoxicity Detection Kit) was added to each well and the plate was incubated at room temperature for 15-30 min in the dark. At the end of the second incubation, the reaction was stopped by adding 50 µl of Stop solution (provided in the Cytotoxicity Detection Kit). The absorbance was measured at the wavelength of 490-492 nm on SPECTRA-MAX™ Plus plate reader (Molecular Devices, Sunnyvale, CA). CDC % was calculated using ([Antibody induced release]−[Spontaneous release control])/([Maximal release]−[spontaneous release control])×100%.

7.4.2. Results

The CDC activity of 15A7H was tested under conditions optimized for CDC response of anti-CD20 with the Ramos cells. As shown in FIG. 6 and Table 11, different concentrations of antibodies with fixed complement dilution of 1:12 were tested for CDC activity. No CDC activity was detected for 15A7H, h15A7 or for the IgG4 negative control. Mouse anti-human CD20 demonstrated a clear antibody dose response.

TABLE 11

Percent CDC activity of 15A7H at different concentrations

| Antibody conc. (µg/ml) | h15A7 | IgG4 Kappa | Mouse anti-CD20 | 15A7H |
|---|---|---|---|---|
| 5 | 1.54 | −0.87 | na | −0.45 |
| 0.5 | 4.25 | 0.50 | 68.26 | −0.15 |
| 0.05 | 0.84 | 3.22 | 59.60 | −2.59 |
| 0.005 | 2.08 | 3.29 | 31.42 | −1.37 |
| 0.0005 | na | na | 6.77 | na |

7.4.3. Conclusion

15A7H shows no CDC activity up to the concentration of 5 µg/ml antibody at the complement dilution of 1:12 in the assays performed on Ramos cells.

7.5 Example 5: Clinical Study

15A7H is given to subjects by intravenous administration of single rising doses of 125 g/kg, 500 µg/kg, 1000 µg/kg and 2000 µg/kg and in other subjects by subcutaneous administration of single doses of 500 µg/kg and 1000 µg/kg. Dosing is adapted. 15A7H resuspended in the formulation described in Table 6 is used. After administration, clinical laboratory tests (e.g., haematology, clinical chemistry and urinalysis) are conducted, for example on a weekly basis, using methods know in the art. Pharmacokinetic parameters are also determined, for example on a weekly basis, using methods know in the art.

All publications, patents, and patent applications cited in this application are hereby incorporated by reference in their entireties as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

What is claimed:

1. A method for treating graft-versus-host disease (GVHD), psoriatic arthritis, or ulcerative colitis, the method comprising injecting into to a human subject in need thereof a pharmaceutical composition comprising:
   (i) a monoclonal antibody which immunospecifically binds to human PSGL-1 comprising:
      (a) a light chain comprising a variable light ("VL") chain region comprising the amino acid sequence of SEQ ID NO: 3;
      (b) a heavy chain comprising variable heavy ("VH") chain region comprising the amino acid sequence of SEQ ID NO: 4; and
      (c) a human IgG4 constant region which contains a Serine to Proline substitution at amino acid 228 of the heavy chain numbered according to the EU index; and
   (ii) a pharmaceutically acceptable carrier,
wherein, the pharmaceutical composition comprises less than 1% half antibody molecules, wherein upon administration to the subject, the pharmaceutical composition inhibits T-cell mediated inflammation in the subject, and wherein the monoclonal antibody of the pharmaceutical composition administered to the subject is present at a concentration between 0.03 mg/kg and 10 mg/kg.

2. The method of claim 1, wherein the monoclonal antibody does not interfere with interaction of P-Selectin and PSGL-1 in the subject.

3. The method of claim 1, wherein the monoclonal antibody of the pharmaceutical composition administered to the subject is present at a concentration selected from 0.03 mg/kg, 0.1 mg/kg, 0.3 mg/kg, 1 mg/kg, and 10 mg/kg.

4. The method of claim 1, wherein the light chain comprises the amino acid sequence set forth in SEQ ID NO: 1, and the heavy chain comprises the amino acid sequence set forth in SEQ ID NO: 2.

5. The method of claim 1, wherein the light chain consists of the amino acid sequence set forth in SEQ ID NO: 1, and the heavy chain consists of the amino acid sequence set forth in SEQ ID NO: 2.

* * * * *

SEQUENCE LISTING

```
<160> NUMBER OF SEQ ID NOS: 21

<210> SEQ ID NO 1
<211> LENGTH: 219
<212> TYPE: PRT
<213> ORGANISM: Artificial Sequence
```

```
<220> FEATURE:
<223> OTHER INFORMATION: 15A7H Light Chain amino acid sequence

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Asn
            20                  25                  30

Asp Gly Asn Thr Tyr Phe Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr His Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Tyr Val Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 2
<211> LENGTH: 447
<212> TYPE: PRT
<213> ORGANISM: Artificial Sequence
<220> FEATURE:
<223> OTHER INFORMATION: 15A7H Heavy Chain amino acid sequence

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Asn Gly Gly Ser Thr Ile Phe Tyr Ala Asn Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ala Ser Tyr Gly Gly Gly Ala Met Asp Tyr Trp Gly Gln
            100                 105                 110

Gly Thr Leu Val Thr Val Ser Ser Ala Ser Thr Lys Gly Pro Ser Val
```

```
            115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly Lys
        435                 440                 445

<210> SEQ ID NO 3
<211> LENGTH: 113
<212> TYPE: PRT
<213> ORGANISM: Artificial Sequence
<220> FEATURE:
<223> OTHER INFORMATION: 15A7H Variable Light Chain Region (VL) amino
      acid sequence

<400> SEQUENCE: 3

Asp Ile Gln Met Thr Gln Ser Pro Ser Ser Leu Ser Ala Ser Val Gly
1               5                   10                  15
Asp Arg Val Thr Ile Thr Cys Arg Ser Ser Gln Ser Ile Val His Asn
            20                  25                  30
```

```
Asp Gly Asn Thr Tyr Phe Glu Trp Tyr Gln Gln Lys Pro Gly Lys Ala
            35                  40                  45

Pro Lys Leu Leu Ile Tyr Lys Val Ser Asn Arg Phe Ser Gly Val Pro
 50                  55                  60

Ser Arg Phe Ser Gly Ser Gly Ser Gly Thr His Phe Thr Leu Thr Ile
 65                  70                  75                  80

Ser Ser Leu Gln Pro Glu Asp Phe Ala Thr Tyr Tyr Cys Phe Gln Gly
                 85                  90                  95

Ser Tyr Val Pro Leu Thr Phe Gly Gln Gly Thr Lys Val Glu Ile Lys
                100                 105                 110

Arg

<210> SEQ ID NO 4
<211> LENGTH: 120
<212> TYPE: PRT
<213> ORGANISM: Artificial Sequence
<220> FEATURE:
<223> OTHER INFORMATION: 15A7H Variable Heavy Chain Region (VH) amino
      acid sequence

<400> SEQUENCE: 4

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
            35                  40                  45

Ala Tyr Ile Asn Gly Gly Ser Ser Thr Ile Phe Tyr Ala Asn Ala Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Ala Ser Tyr Gly Gly Gly Ala Met Asp Tyr Trp Gly Gln
                100                 105                 110

Gly Thr Leu Val Thr Val Ser Ser
        115                 120

<210> SEQ ID NO 5
<211> LENGTH: 16
<212> TYPE: PRT
<213> ORGANISM: Artificial Sequence
<220> FEATURE:
<223> OTHER INFORMATION: 15A7H VL CDR1 amino acid sequence

<400> SEQUENCE: 5

Arg Ser Ser Gln Ser Ile Val His Asn Asp Gly Asn Thr Tyr Phe Glu
 1               5                  10                  15

<210> SEQ ID NO 6
<211> LENGTH: 7
<212> TYPE: PRT
<213> ORGANISM: Artificial Sequence
<220> FEATURE:
<223> OTHER INFORMATION: 15A7H VL CDR2 amino acid sequence

<400> SEQUENCE: 6

Lys Val Ser Asn Arg Phe Ser
 1               5
```

```
<210> SEQ ID NO 7
<211> LENGTH: 9
<212> TYPE: PRT
<213> ORGANISM: Artificial Sequence
<220> FEATURE:
<223> OTHER INFORMATION: 15A7H VL CDR3 amino acid sequence

<400> SEQUENCE: 7

Phe Gln Gly Ser Tyr Val Pro Leu Thr
1               5

<210> SEQ ID NO 8
<211> LENGTH: 5
<212> TYPE: PRT
<213> ORGANISM: Artificial Sequence
<220> FEATURE:
<223> OTHER INFORMATION: 15A7H VH CDR1 amino acid sequence

<400> SEQUENCE: 8

Ser Phe Gly Met His
1               5

<210> SEQ ID NO 9
<211> LENGTH: 17
<212> TYPE: PRT
<213> ORGANISM: Artificial Sequence
<220> FEATURE:
<223> OTHER INFORMATION: 15A7H VH CDR2 amino acid sequence

<400> SEQUENCE: 9

Tyr Ile Asn Gly Gly Ser Ser Thr Ile Phe Tyr Ala Asn Ala Val Lys Gly
1               5                   10                  15

<210> SEQ ID NO 10
<211> LENGTH: 11
<212> TYPE: PRT
<213> ORGANISM: Artificial Sequence
<220> FEATURE:
<223> OTHER INFORMATION: 15A7H VH CDR3 amino acid sequence

<400> SEQUENCE: 10

Tyr Ala Ser Tyr Gly Gly Gly Ala Met Asp Tyr
1               5                   10

<210> SEQ ID NO 11
<211> LENGTH: 412
<212> TYPE: PRT
<213> ORGANISM: Homo sapiens
<220> FEATURE:
<223> OTHER INFORMATION: Full length human PSGL-1 amino acid sequence

<400> SEQUENCE: 11

Met Pro Leu Gln Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
                20                  25                  30

Gly Pro Leu Leu Ala Arg Asp Arg Arg Gln Ala Thr Glu Tyr Glu Tyr
            35                  40                  45

Leu Asp Tyr Asp Phe Leu Pro Glu Thr Glu Pro Pro Glu Met Leu Arg
    50                  55                  60

Asn Ser Thr Asp Thr Thr Pro Leu Thr Gly Pro Gly Thr Pro Glu Ser
65                  70                  75                  80

Thr Thr Val Glu Pro Ala Ala Arg Arg Ser Thr Gly Leu Asp Ala Gly
                85                  90                  95
```

```
Gly Ala Val Thr Glu Leu Thr Thr Glu Leu Ala Asn Met Gly Asn Leu
                100                 105                 110
Ser Thr Asp Ser Ala Ala Met Glu Ile Gln Thr Thr Gln Pro Ala Ala
            115                 120                 125
Thr Glu Ala Gln Thr Thr Gln Pro Val Pro Thr Glu Ala Gln Thr Thr
        130                 135                 140
Pro Leu Ala Ala Thr Glu Ala Gln Thr Thr Arg Leu Thr Ala Thr Glu
145                 150                 155                 160
Ala Gln Thr Thr Pro Leu Ala Ala Thr Glu Ala Gln Thr Thr Pro Pro
                165                 170                 175
Ala Ala Thr Glu Ala Gln Thr Thr Gln Pro Thr Gly Leu Glu Ala Gln
            180                 185                 190
Thr Thr Ala Pro Ala Ala Met Glu Ala Gln Thr Thr Ala Pro Ala Ala
        195                 200                 205
Met Glu Ala Gln Thr Thr Pro Pro Ala Ala Met Glu Ala Gln Thr Thr
210                 215                 220
Gln Thr Thr Ala Met Glu Ala Gln Thr Thr Ala Pro Glu Ala Thr Glu
225                 230                 235                 240
Ala Gln Thr Thr Gln Pro Thr Ala Thr Glu Ala Gln Thr Thr Pro Leu
                245                 250                 255
Ala Ala Met Glu Ala Leu Ser Thr Glu Pro Ser Ala Thr Glu Ala Leu
            260                 265                 270
Ser Met Glu Pro Thr Thr Lys Arg Gly Leu Phe Ile Pro Phe Ser Val
        275                 280                 285
Ser Ser Val Thr His Lys Gly Ile Pro Met Ala Ala Ser Asn Leu Ser
290                 295                 300
Val Asn Tyr Pro Val Gly Ala Pro Asp His Ile Ser Val Lys Gln Cys
305                 310                 315                 320
Leu Leu Ala Ile Leu Ile Leu Ala Leu Val Ala Thr Ile Phe Phe Val
                325                 330                 335
Cys Thr Val Val Leu Ala Val Arg Leu Ser Arg Lys Gly His Met Tyr
            340                 345                 350
Pro Val Arg Asn Tyr Ser Pro Thr Glu Met Val Cys Ile Ser Ser Leu
        355                 360                 365
Leu Pro Asp Gly Gly Glu Gly Pro Ser Ala Thr Ala Asn Gly Gly Leu
370                 375                 380
Ser Lys Ala Lys Ser Pro Gly Leu Thr Pro Glu Pro Arg Glu Asp Arg
385                 390                 395                 400
Glu Gly Asp Asp Leu Thr Leu His Ser Phe Leu Pro
                405                 410

<210> SEQ ID NO 12
<211> LENGTH: 13
<212> TYPE: PRT
<213> ORGANISM: Artificial Sequence
<220> FEATURE:
<223> OTHER INFORMATION: IgG4 hinge region amino acid sequence

<400> SEQUENCE: 12

Glu Ser Lys Tyr Gly Pro Pro Cys Pro Pro Cys Pro Ala
1               5                   10

<210> SEQ ID NO 13
<211> LENGTH: 23
<212> TYPE: PRT
<213> ORGANISM: Artificial Sequence
<220> FEATURE:
```

<223> OTHER INFORMATION: 15A7H VL FR1

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 14
<211> LENGTH: 15
<212> TYPE: PRT
<213> ORGANISM: Artificial Sequence
<220> FEATURE:
<223> OTHER INFORMATION: 15A7H VL FR2

<400> SEQUENCE: 14

Trp Tyr Gln Gln Lys Pro Gly Lys Ala Pro Lys Leu Leu Ile Tyr
1               5                   10                  15

<210> SEQ ID NO 15
<211> LENGTH: 32
<212> TYPE: PRT
<213> ORGANISM: Artificial Sequence
<220> FEATURE:
<223> OTHER INFORMATION: 15A7H VL FR3

<400> SEQUENCE: 15

Gly Val Pro Ser Arg Phe Ser Gly Ser Gly Ser Gly Thr His Phe Thr
1               5                   10                  15

Leu Thr Ile Ser Ser Leu Gln Pro Glu Asp Phe Ala Thr Tyr Tyr Cys
            20                  25                  30

<210> SEQ ID NO 16
<211> LENGTH: 11
<212> TYPE: PRT
<213> ORGANISM: Artificial Sequence
<220> FEATURE:
<223> OTHER INFORMATION: 15A7H VL FR4

<400> SEQUENCE: 16

Phe Gly Gln Gly Thr Lys Val Glu Ile Lys Arg
1               5                   10

<210> SEQ ID NO 17
<211> LENGTH: 30
<212> TYPE: PRT
<213> ORGANISM: Artificial Sequence
<220> FEATURE:
<223> OTHER INFORMATION: 15A7H VH FR1

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 18
<211> LENGTH: 14
<212> TYPE: PRT
<213> ORGANISM: Artificial Sequence
<220> FEATURE:
<223> OTHER INFORMATION: 15A7H VH FR2

<400> SEQUENCE: 18

Trp Val Arg Gln Ala Pro Gly Lys Gly Leu Glu Trp Val Ala

```
<210> SEQ ID NO 19
<211> LENGTH: 32
<212> TYPE: PRT
<213> ORGANISM: Artificial Sequence
<220> FEATURE:
<223> OTHER INFORMATION: 15A7H VH FR3

<400> SEQUENCE: 19

Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 20
<211> LENGTH: 11
<212> TYPE: PRT
<213> ORGANISM: Artificial Sequence
<220> FEATURE:
<223> OTHER INFORMATION: 15A7H VH FR4

<400> SEQUENCE: 20

Trp Gly Gln Gly Thr Leu Val Thr Val Ser Ser
1               5                   10

<210> SEQ ID NO 21
<211> LENGTH: 13
<212> TYPE: PRT
<213> ORGANISM: Homo sapiens
<220> FEATURE:
<223> OTHER INFORMATION: IgG4 wild-type hinge region amino acid sequence

<400> SEQUENCE: 21

Glu Ser Lys Tyr Gly Pro Pro Cys Pro Ser Cys Pro Ala
1               5                   10
```